US009115342B2

(12) United States Patent
Hattori et al.

(10) Patent No.: US 9,115,342 B2
(45) Date of Patent: Aug. 25, 2015

(54) METHOD FOR PURIFYING CARDIOMYOCYTES OR PROGRAMMED CARDIOMYOCYTES DERIVED FROM STEM CELLS OR FETUSES

(75) Inventors: Fumiyuki Hattori, Mitaka (JP); Keiichi Fukuda, Tokyo (JP)

(73) Assignees: DAIICHI SANKYO COMPANY, Tokyo (JP); KEIO UNIVERSITY, Tokyo (JP)

(*) Notice: Subject to any disclaimer, the term of this patent is extended or adjusted under 35 U.S.C. 154(b) by 621 days.

(21) Appl. No.: 12/162,684

(22) PCT Filed: Jan. 31, 2007

(86) PCT No.: PCT/JP2007/051563
§ 371 (c)(1),
(2), (4) Date: Feb. 6, 2009

(87) PCT Pub. No.: WO2007/088874
PCT Pub. Date: Aug. 9, 2007

(65) Prior Publication Data
US 2009/0275132 A1 Nov. 5, 2009

(30) Foreign Application Priority Data
Jan. 31, 2006 (JP) ................................ 2006-023770

(51) Int. Cl.
*C12N 5/077* (2010.01)
(52) U.S. Cl.
CPC .......... *C12N 5/0657* (2013.01); *C12N 2500/02* (2013.01); *C12N 2500/14* (2013.01); *C12N 2500/25* (2013.01); *C12N 2500/32* (2013.01); *C12N 2500/34* (2013.01); *C12N 2500/38* (2013.01); *C12N 2500/44* (2013.01); *C12N 2500/99* (2013.01); *C12N 2501/115* (2013.01); *C12N 2501/235* (2013.01); *C12N 2501/70* (2013.01); *C12N 2506/02* (2013.01)

(58) Field of Classification Search
CPC .......................... C12N 5/0657; C12N 2506/02
See application file for complete search history.

(56) References Cited

U.S. PATENT DOCUMENTS

| 2002/0168763 | A1 | 11/2002 | Yan et al. | |
| 2005/0054092 | A1* | 3/2005 | Xu et al. | 435/366 |

FOREIGN PATENT DOCUMENTS

| EP | 1 254 952 | 11/2002 |
| WO | WO 00/49137 | 8/2000 |
| WO | WO 01/48151 | 7/2001 |
| WO | 2005/090558 | 9/2005 |
| WO | 2005/118784 | 12/2005 |
| WO | WO 2006/066320 A1 | 6/2006 |

OTHER PUBLICATIONS

Stem Cells: Scientific Progress and Future Research Directions. Department of Health and Human Services. Jun. 2001. ,/info/scireport/2001report>. Chapter 4: The Adult Stem Cell. pp. 23-42.*
Xu et al., "Characterization and Enrichment of Cardiomyocytes Derived from Human Embryonic Stem Cells," *Circulation Research*, Grune and Stratton, Baltimore, MD, vol. 91, No. 6, Sep. 20, 2002, pp. 501-508.
Passier et al., "Increased Cardiomyocyte Differentiation from Human Embryonic Stem Cells in Serum Free Cultures," *Stem Cells*, Alphamed Press, Dayton, OH, vol. 23, Jan. 1, 2005, pp. 772-780.
European Search Report issued in European Patent Application No. EP 07713734.7 mailed May 14, 2009.
Mark C. Fishman, "Zebrafish—The Canonical Vertebrate", *Science*, Nov. 9, 2001, vol. 294, pp. 1290-1291.
Hidaka et al., "Chamber-specific differentiation of Nkx2.5-positive cardiac precursor cells from murine embryonic stem cells", *FASEB Journal*, Apr. 2003, vol. 17, pp. 740-742.
Hwang, et al., "Evidence of a pluripotent human embryonic stem cell line derived from a cloned blastocyst", *Science*, Mar. 12, 2004, vol. 303; pp. 1669-1674.
Makino et al., "Cardiomyocytes can be generated from marrow stromal cells in vitro", *J. Clinical Investigation*, Mar. 1999, vol. 103, No. 5, pp. 697-705.
Mitalipova et al., "Pluripotency of bovine embryonic cell line derived from precompacting embryos", *Cloning*, vol. 3, No. 2, 2001, pp. 59-67.
Munsie et al., "Isolation of pluripotent embryonic stem cells from reprogrammed adult mouse somatic cell nuclei", *Current Biology*, vol. 10, No. 16, 2000, pp. 989-992.
Petitte et al., "Avian pluripotent stem cells", *Mechanisms of Development*, vol. 121, 2004, pp. 1159-1168.
Sasaki et al., "Establishment of novel embryonic stem cell lines derived from the common marmoset (*Callithrix jacchus*)", *Stem Cells*, 2005, vol. 23, pp. 1304-1313.
Suemori et al., "Establishment of Embryonic Stem Cell Lines from Cynomolgus Monkey Blastocyts Produced by IVF or ICSI", *Developmental Dynamics*, 2001, vol. 222, pp. 273-279.
Suemori et al., "Efficient establishment of human embryonic stem cell lines and long-term maintenance with stable karyotype by enzymatic bulk passage",Biochemical and Biophysical Research Communications, vol. 345, (2006), pp. 926-932.
Tada et al., "Nuclear reprogramming of somatic cells by in vitro hybridization with ES cells", *Current Biology*, 2001, vol. 11, pp. 1553-1558.
Thomson et al., "Isolation of a primate embryonic stem cell line", *Proc. Nat. Acad. Sci.*, Aug. 1995, vol. 92, pp. 7844-7848.

(Continued)

*Primary Examiner* — Marcia S Noble
(74) *Attorney, Agent, or Firm* — Drinker Biddle & Reath LLP

(57) ABSTRACT

An object of the present invention is to develop a method for purify cardiomyocytes at a high degree of purification and at a high yield from a cell mixture comprising cardiomyocytes derived from fetuses and stem cells using various features which have not been previously expected to be used for purification of cardiomyocytes or which are newly found, wherein said method is carried out without undergoing any genetic modification or without adding any special proteins or biologically active agents.

18 Claims, 19 Drawing Sheets

(56) References Cited

OTHER PUBLICATIONS

Vrana et al., "Nonhuman primate parthenogenetic stem cells", *Proc. Nat. Acad. Sci*, Sep. 30, 2003, vol. 100, Suppl. 1, pp. 11911-11916.
Wakayama et al., "Differentiation of Embryonic Stem Cell Lines Generated from AdultSomatic Cells by Nuclear Transfer", *Science*, Apr. 27, 2001, vol. 292, pp. 740-743.
Bader et al., "Paracrine promotion of cardiomyogenesis in embryoid bodies of LIF modulated endoderm", *Differentiation* (2001), vol. 68, pp. 31-43.
Fijnvandraat et al., "Cardiomyocytes purified from differentiated embryonic stem cells exhibit characteristics of early chamber myocardium", *J. Molecular and Cellular Cardiology*, vol. 35 (2003) pp. 1461-1472.
Honda, et al., "RXR agonist enhances the differentiation of cardiomyocytes derived from embryonic stem cells in serum-free conditions," Biochemical and Biophysical Research Communications 333 (2005) pp. 1334-1340.
European Search Report mailed May 25, 2012, issued in European Application No. EP 12 16 0317.
Invitation to Respond to Written Opinion, Search Report and Written Opinion mailed Oct. 24, 2014 by Intellectual Property Office of Singapore in Singapore Patent Application No. 2011006582, 16 pages.
Boheier, et al., "Differentiation of Pluripotent Embryonic Stem Cells Into Cardiomyocytes", Circulation Research, Aug. 9, 2002, vol. 81, No. 3, pp. 189-201.
Passier, et al., "Cardiomyocytes differentiation from embryonic and adult stem cells", Current Opinion in Biotechnology, Aug. 11, 2005, vol. 16, No. 5, pp. 498-502.
Tohyama, et al., "Distinct Metabolic Flow Enables Large-Scale Purification of Mouse and Human Pluripotent Stem Cell-Dervied Cardiomyocytes", Cell Stem Cell, Nov. 15, 2002, vol. 12, No. 1, pp. 127-137.
Pieter A. Doevendans et al., "Differentiation of Cardiomyocytes in Floating Embryoid Bodies is Comparable to Fetal Cardiomyocytes", J. Mol. Cell Cardiol., 2000, pp. 839-851, vol. 32.
International Search Report mailed Feb. 27, 2007 in International Application No. PCT/JP2007/051563 filed Jan. 31, 2007.
Müller et al., "Selection of ventricular-like cardiomyocytes from ES cells in vitro," FASEB J. 2000, vol. 14, pp. 2540-2548.
Klug et al., "Genetically Selected Cardiomyocytes from Differentiating Embryonic Stem Cells Form Stable Intracardiac Grafts," J. Clin. Invest., vol. 98, No. 1, Jul. 1996, pp. 216-224.
Schröder, et al., "HIV-1 Integration in the Human Genome Favors Active Genes and Local Hotspots," Cell, vol. 110, Aug. 23, 2002, pp. 521-529.
Khairallah et al., "Profiling substrate fluxes in the isolated working mouse heart using $^{13}C$-labeled substrates: focusing on the origin and fate of pyruvate and citrate carbons," Am. J. Physiol. Heart Circ. Physiol., 2004, vol. 286, pp. H1461-H1470.
Chatham et al., Calculation of Absolute Metabolic Flux and the Elucidation of the Pathways of Glutamate Labeling in Perfused Rat Hears by $^{13}C$ NMr Spectroscopy and Nonlinear Least Squares Analysis, The Journal of Biological Chemistry, Apr. 7, 1995, vol. 270, No. 14, pp. 7999-8008.

\* cited by examiner

A. Before selection

B. After selection: Bright field image

C. After selection:
Sarcomere-Actinin fluorescent immunostaining image

A

B

METHOD FOR PURIFYING CARDIOMYOCYTES OR PROGRAMMED CARDIOMYOCYTES DERIVED FROM STEM CELLS OR FETUSES

CROSS REFERENCE TO RELATED APPLICATIONS

This application is the national stage of International Application No. PCT/JP2007/051563, filed Jan. 31, 2007, and claims benefit of Japanese Application No. 2006-23770, filed Jan. 31, 2006, both of which are herein incorporated by reference in their entirety.

TECHNICAL FIELD

The present invention relates to a method for purifying cardiomyocytes from a cell population derived from stem cells and fetuses and also to a method for using thereof.

BACKGROUND ART

Since a cardiomyocyte loses a proliferative ability in an adult body, it is necessary to conduct heart transplantation in treating a serious heart disease such as cardiac infarction or cardiomyopathy. However, currently, since insufficient donor hearts are available, there is now a pressing need to develop a method of treatment other than heart transplantation.

On the other hand, the recruitment of the ex vivo produced cardiomyocytes is expected to be a most promising method of providing relief for patients in need of heart transplantation. Various methods of preparing cardiomyocytes have been investigated, such as a method of differentiating stem cells (embryonic stem cells or various adult stem cells) into cardiomyocytes or a method for isolating cardiomyocytes from fetuses.

The differentiation of the cardiomyocytes from the embryonic stem cells are positively induced through formation of a cell mass (an embryoid body) by eliminating from culture medium differentiation suppression factors (such as feeder cells, leukemia inhibitory factor: LIF) in the case of mouse embryonic stem cells or differentiation suppression factors (such as feeder cells, basic fibroblast growth factor: bFGF, transforming growth factor: TGF) in the case of human embryonic stem cells.

A mode of in vitro differentiation partially follows a mode of physiological development. Especially, relating to the events of early development, there are a number of commonalities between the mode of physiological development in fertilized egg cells and the mode of in vitro differentiation. In their vitro cardiomyocyte differentiation course, as is also in physiological development, undifferentiated mesoblast cells are first generated, a part of which is changed to programmed cardiomyocytes (pre-cardiac mesoblast cells) and then differentiated into the cardiomyocytes. However, since the embryonic stem cells can differentiate into any types of cells which construct an organ within a body, it is technically difficult to differentiate the embryonic stem cells into only a single type of cell.

Further, since it is also difficult under non-physiological condition (in vitro) to induce differentiation of the embryonic stem cells into all types of cells, there partially remains the undifferentiated cells. Moreover, the mesenchymal stem cells present in bone marrow or umbilical cord and tissue stem cells present in various kinds of tissues (such as neural stem cell, adipose derived stem cells, and skeletal muscle stem cells) are considered to be the adult stem cells, which are considered to have an ability to differentiate into the cardiomyocytes. These cells are believed to differentiate not only into the cardiomyocytes but also into various kinds of cells. Though the details of differentiation mechanisms from any of the adult stem cells to the cardiomyocytes have not been fully elucidated, it is known that these cells form the cardiomyocytes, other differentiated cells, and a cell population containing undifferentiated cells after undergoing a certain period of transition phase.

In summary, all stem cells cause some common deleterious characteristics for clinical application that there are cells other than the cardiomyocytes which are generated from the stem cells as a by-products or undifferentiated cells. Since the undifferentiated cells have a proliferative activity and have an ability to differentiate into many types of cells, a cell population containing the cardiomyocytes generated by differentiation induction can not be transplanted into a living body in the therapy.

Therefore, to safely implement the treatment using stem cells and achieve an ideal treatment effect, it is necessary to develop a method for purifying the cardiomyocytes from the cell population.

To date, the cardiomyocytes have been purified by a method for purifying the cardiomyocytes by specifically expressing a fluorescent marker such as GFP in the cardiomyocytes and selecting a cell expressing a fluorescent marker using cell sorter (Non-patent document 1) or a method for purifying the cardiomyocytes by specifically expressing an antibiotic resistant protein in the cardiomyocytes and selecting the cells using the antibiotic (Non-patent document 2). However, since these methods have to involve in a genetic alteration, which cause an issue relating to the safety, these methods can not be used to prepare the cardiomyocytes for transplantation in the clinical field. Further, since these methods involve in a genetic alteration, an ethical issue and some unpredictable serious risk such as the change in the rate of transformation are associated with a genomic alteration (Non-patent document 3), It is known in the art that the heart can use a lactic acid generated by a tissue other than the heart (such as skeletal muscle) as an energy source (Non-patent document 4). However, there are no prior art to attempt to purify cardiomyocytes using this feature.

Also, in the heart, the liver, and the kidney, an aspartic acid and a glutamic acid are used for transporting NADH into mitochondria, the mechanism of which is different from that of the other tissue (Non-patent document 5). The transportation of NADH into mitochondria is indispensable for an energy production in mitochondria. However, there are no prior art to attempt to purify cardiomyocytes using this difference in this mechanism.

Non-patent document 1: Muller M, et al., FASEB J. 2000; 14: 2540-2548
Non-patent document 2: Klug MG, et al., J. Clin. Invest. 1996; 98: 216-224
Non-patent document 3: Schroder AR, et al., Cell. 2002; 110: 521-529
Non-patent document 4: Khairallah M, et al., Am J Physiol Heart Circ Physiol 2004; 286, H1461-1470
Non-patent document 5: Chatham J C, et al., J Biol Chem 1995; 270: 7999-8008

DISCLOSURE OF THE INVENTION

A Problem To Be Solved By The Invention

An object of the present invention is to develop a method for purify cardiomyocytes at a high degree of purification and at a high yield from a cell mixture comprising cardiomyocytes derived from fetuses and stem cells using various features which have not been previously expected to be used for purification of cardiomyocytes or which are newly found, wherein said method is carried out without undergoing any genetic alteration or without adding any special proteins or biologically active agents.

Means For Solving The Problem

The inventors of the present invention conducted an exhaustive study for the compositions of various kinds of culture medium, in order to construct a system for efficiently producing cardiomyocytes derived from embryonic stem cells. Based on the results regarding a study for a concentration of each components of various culture medium or a study for the timing of changes in a concentration of each components of various culture medium obtained by changing compositions of components of various culture medium, the inventors of the present invention found the following events:

(1) An event in which an inhibition of cell differentiation/growth and an induction of non-cardiomyocyte-directed cell death occur, when a cell mixture containing the cardiomyocytes and the non-cardiomyocytes are cultured in a low-serum-supplemented condition or a serum-free condition;

(2) An event in which an induction of non-cardiomyocyte-directed cell death occurs, when a cell mixture containing the cardiomyocytes and the non-cardiomyocytes are cultured in a mildly-acidic culture medium;

(3) An event in which an inhibition of cell differentiation/growth and an induction of non-cardiomyocyte-directed cell death occurs, when a cell mixture containing the cardiomyocytes and the non-cardiomyocytes are cultured in a low calcium culture medium;

(4) An event in which non-cardiomyocytes selectively undergo cell death, when the cardiomyocytes are cultured in a low-nutritional culture medium;

(5) An event in which energy consumption is inhibited by weakening autonomous pulsating of cardiomyocytes, when the cardiomyocytes are cultured in a low calcium condition;

(6) An event in which a spontaneous cell mass formation of cardiomyocytes is enhanced under a low-serum-supplemented condition or serum-free condition; and (7) An event in which a viability of a cardiomyocyte is significantly reduced when the cardiomyocytes are cultured after dispersing a cell mass of the cardiomyocytes.

The inventors of the present invention found that cardiomyocytes derived from the embryonic stem cells can be selected or purified efficiently and at a high degree by optimized method using one or more processes corresponding to these events. Further, the inventors also found that the methods developed from the properties of the embryonic stem cells are also applicable to select or purify cardiomyocytes derived from fetuses or to select or purify cardiomyocytes derived from the adult stem cells. Based on these findings, the inventors have completed the present invention.

More specifically, in one embodiment, the present invention provides a method for selecting cardiomyocytes from a cell mixture containing cardiomyocytes and non-cardiomyocytes derived from embryonic stem cells, adult stem cells or fetuses, wherein said cell mixture is cultured in the culture medium under the following conditions: (i) a low-sugar-supplemented condition; and (ii) one or more conditions selected from the group consisting of a low calcium condition, a low-nutritional condition, a lactic acid-supplemented condition, an aspartic acid/glutamic acid-supplemented condition, and a pyruvic acid-supplemented condition. In this embodiment, the cell mixture can be prepared by inducing differentiation of embryonic stem cells, forming embryoid bodies comprising programmed cardiomyocytes (undifferentiated mesoblast cell), culturing the embryoid bodies in the culture medium under a low-serum-supplemented condition and/or a mildly-acidic pH condition.

In another embodiment, the present invention provides a method for selecting cardiomyocytes derived from embryonic stem cells, wherein the cardiomyocytes are selected by the following steps of: inducing differentiation of embryonic stem cells to form embryoid bodies comprising undifferentiated mesoblast cells; then culturing the embryoid bodies in the culture medium under a low-serum-supplemented condition and/or a mildly-acidic pH condition to prepare a cell mixture comprising programmed cardiomyocytes; and continuing the culture of the cell mixture in the same culture medium to obtain the cardiomyocytes.

BRIEF DESCRIPTION OF THE DRAWINGS

FIG. 6-1 shows an analysis of programmed cardiomyocytes within the mass of the embryonic stem cells under a serum-free/mildly-acidic pH condition.

FIG. 6-2 shows an analysis of programmed cardiomyocytes within the mass of the embryonic stem cells under a serum-free/mildly-acidic pH condition.

FIG. 12-1 shows masses of the cardiomyocytes selected by culturing the cells under a serum-free/mildly-acidic/low calcium/sugar-free and a lactic acid-supplemented condition.

FIG. 12-2 shows masses of the cardiomyocytes selected by culturing the cells under a serum-free/mildly-acidic/low calcium/sugar-free and a lactic acid-supplemented condition.

EMBODIMENTS OF THE INVENTION

Figure 1:
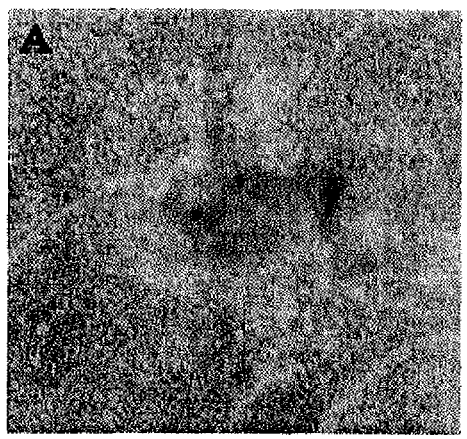
FIG. 1 shows a mode of presentation of the cardiomyocytes within an embryoid body after adhesion culture.
Figure 1:
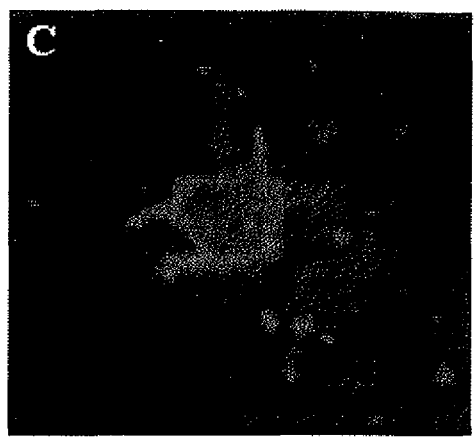
Figure 1:
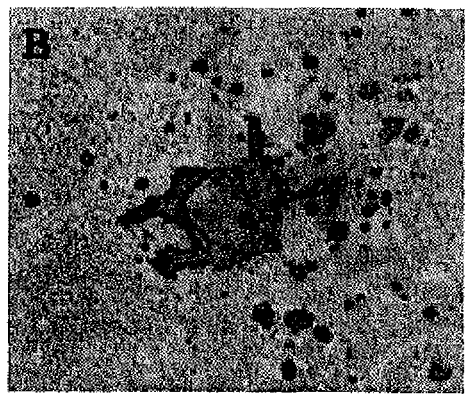
Figure 1:
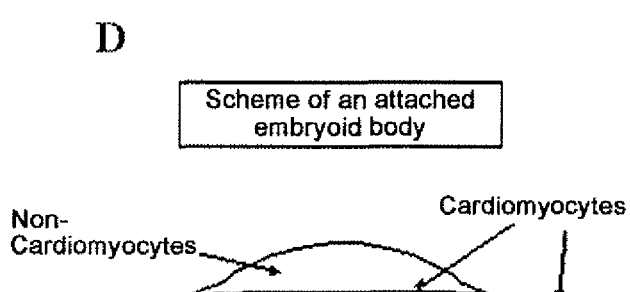

An appropriate treatment for inducing cardiomyocyte differentiation generally causes differentiation of the stem cells having an ability to differentiate into the cardiomyocytes (i.e., embryonic stem cells and adult stem cells such as bone marrow stem cells) into the cardiomyocytes. It is possible to induce differentiation of the embryonic stem cells into the cardiomyocytes using hanging drop method, in which, for example, the mouse embryonic stem cells are incubated in the suspension culture under a condition in the absence of leukemia inhibitory factor (LIF) to form a cell mass (an embryoid body). Also, in the same manner, the marmoset embryonic stem cells or the human embryonic stem cells can be used to induce differentiation of the embryonic stem cells into the cardiomyocytes.

The present method can be applied to stem cells derived from any mammalian species. For example, the examples of the mammalian species from which stem cells are derived, used in the present method, include, but not limited to, mouse, cow, goat, dog, cat, marmoset, rhesus monkey, human and so on. The examples of the stem cells used for the present invention include mammalian ES cells which are widely used in the art such as mouse ES cells, monkey ES cells, and human ES cells.

The specific examples of the mouse ES cells include EB3 cells, E14 cells, D3 cells, CCE cells, R1 cells, 1295V cells, J1 cells, and so on. The mouse ES cells used for the present invention are available from American Type Culture Collection (ATCC), Chemicon, and Cell & Molecular Technologies, and so on.

The examples of the monkey ES cells include ES cells established from rhesus monkey (*Macaca mulatta*) (Thomson et al., Proc. Natl. Acad. Sci. USA 1995; 92: 7844), ES cells established from cynomolgus monkey (*Macaca fascicularis*) (Suemori et al., Dev. Dyn. 2001; 222: 273-279) and ES cells established common marmoset (*Callithrix jacchus*) (Sasaki et al., Stem Cells, 2005; 23: 1304-1313), which are all available in the art. For example, the marmoset ES cells are available from Central Institute for Experimental Animals (Kawasaki, Japan).

To date, several dozen kinds of human ES cells have been established in the world, and a number of human ES cell lines are registered on the list of the United States National Institute of Health (http://stemcells.nih.gov/registry/index.asp) and are available. In the United States, some human ES cell lines are also commercially available from Cellartis, ES Cell international, Wisconsin Alumni Research Foundation, and so on. Also in Japan, some human ES cell lines are available from the Stem Cell Research Center (the Institute for Frontier medical Sciences, Kyoto University) (Suemori et al., Biochem. Biophys. Res. Commun., 2006; 345: 926-932).

Further, cow ES cells (Mitalipova et al., Cloning 2001; 3: 59-67), chicken ES cells (Petitte et al., Mech. Dev. 2004; 121: 1159-1168), and zebrafish ES cells (Fishman, M. C., Science 2001; 294: 1290-1291) have also been established.

Generally, ES cells are established by culturing an early embryo. In addition to this method, it is possible to produce ES cells from the early embryo which undergoes the nucleus transplantation of the nucleus of the somatic cells (Munsie et al., Curr. Biol. 10: 989, 2000; Wakayama et al., Science 292: 740, 2001; Hwang et al., Science 303: 1669, 2004). There are also some reports attempting to isolate stem cells as follows: a method for producing ES cells from the parthenogenetic embryonic cells which are developed to a stage equivalent to the blastocyst stage (US Patent Publication No. 02-168763; Vrana K et al., Proc. Natl. Acad. Sci. USA 100: 11911-6, 2003) and a method for producing ES cells having genetic information originally contained in the nucleus of somatic cells by fusing the ES cells and the somatic cells (WO 00/49137; Tada et al., Curr. Biol. 11: 1553, 2001). The examples of the ES cells used in the present invention include ES cells prepared by the method described above or cells in which one or more genes on the chromosome of the ES cells are altered by genetic engineering technique.

Further, the examples of the stem cells used in the method of the present invention include not only ES cells but also any stem cells having similar characteristics to those of ES cells, which are derived from cells of the mammalian adult organs or tissues, cells of the bone marrow, blood cells, and cells of embryos or fetuses. In this context, the phrase "similar characteristics to those of ES cells" can be defined by cellular biological characteristics specific for ES cells (such as the presence of a surface (antigen) marker specific for the ES cells, ES cells specific gene expression, or an ability to form a teratoma or a chimeric mouse). The specific examples of the stem cells having similar characteristics to those of the ES cells include EG cells produced from primordial germ cells, GS cells produced from testicular germ cells, and induced pluripotent stem cells (i)PS cells) produced from somatic cells such as fibroblast using special genetic engineering technique. It is considered that, in this method, embryoid bodies after 3-5 days from the start of differentiation induction, conducted by culturing the stem cells by the suspension culture in the absence of LIF, include undifferentiated mesoblast cells and programmed cardiomyocytes which are to differentiate into the cardiomyocytes in the future. It is known in the art that, in the case of inducing the embryonic stem cells, a cardiomyocyte appears after 7 days from the start of differentiation induction (in the case of the human embryonic stem cells, after 10 days from the start of differentiation induction). However, the thus prepared embryoid bodies using the embryonic stem cells include not only the cardiomyocytes described above but also cells which does not have an ability to differentiate into the cardiomyocytes (such as the undifferentiated cells, the endothelium-epithelium like cells, and the neuronal cells). In the present invention, any cells other than the cardiomyocytes or cells which differentiate into the cardiomyocytes in the future (such as undifferentiated mesoblast cell, the programmed cardiomyocytes) are referred to as a "non-cardiomyocyte".

The present inventors studied effects of the culture conditions such as a low-serum-supplemented condition, a low-sugar-supplemented condition, a low-nutritional condition, a low calcium condition, and a mildly-acidic pH condition on selection of the cardiomyocytes, in order to specifically discriminating the cardiomyocytes or cells which differentiate into the cardiomyocytes in the future from non-cardiomyocytes contained within the thus prepared embryoid bodies.

As a result, the present inventors found that when a cell mixture containing the undifferentiated mesoblast cell, the programmed cardiomyocytes and the cardiomyocytes is cultured under one or more conditions which are selected from the group consisting of a low-serum-supplemented condition, a low-sugar-supplemented condition, a low-nutritional condition, a low calcium condition, a mildly-acidic pH condition, alone or in any combination, the cardiomyocytes or cells which differentiate into the cardiomyocytes in the future are less sensitive to cytotoxic effect as compares with the non-cardiomyocytes under such condition.

On the basis of this finding, in the present invention, cells which are viable even under the above conditions were able to be selected as programmed cardiomyocytes and cardiomyocytes from a cell mixture containing the undifferentiated mesoblast cell, the programmed cardiomyocytes and the cardiomyocytes, by culturing the cell mixture under the condition of a low-sugar-supplemented condition in combination with any one or any combinations of a low-serum-supplemented condition, a low-nutritional condition, a low calcium condition and a mildly-acidic pH condition.

The above described selection method is to select the cells of interest by culturing the cell mixture under the condition to which the cardiomyocytes are physiologically resistant, and therefore, is referred to as "physiological resistance-based selection method". The physiological resistance-based selection method of the present invention is characterized by culturing the cell mixture containing the cardiomyocytes in the culture medium under the condition selected from a low-sugar-supplemented condition, a low-serum -supplemented condition, a low-nutritional condition, a low calcium condition, or a mildly-acidic pH condition.

In the present invention, the term "a low-sugar -supplemented condition" is defined to be a condition under which the cell mixture is cultured in the culture medium with reduced level of sugars (i.e., group of substances including polysaccharides and monosaccharides (such as glucose, galactose, fructose, mannose), which are biochemically dissolve and converted in vivo or intracellularly to finally be catabolized by the glycolytic system). In the preferred embodiment, the term "a low-sugar-supplemented condition." means that the cell mixture is cultured in the culture medium in the absence of the sugars above or in the culture medium in which the level of sugars is limited to less than 1% as compared to the level of sugars in the culture medium used for the differentiation induction. In the present invention, it is desirable to eliminate at least glucose, among others, as much as possible from the culture medium. For example, the commercially available culture mediums which are generally used in the art (such as α-MEM, MEM [Hank's BSS], DMEM) contain 1 g/L of D-glucose (5.56 mM), RPMI 1640 contains 2.0 g/L of D-glucose (11.12 mM), and Ham's F-12 contains 1.82 g/L of D-glucose (10.12 mM), respectively, as sugars. Therefore, the culture medium with the level of sugars being reduced to 1% means the culture medium containing 55.60-111.20 µM of sugars.

The present inventors found that, when the cell mixture is cultured in the culture medium under the limited level of sugars to less than 1% as compared to the level of sugars generally used in the art, the non-cardiomyocytes undergo cell death, while the undifferentiated mesoblast cell, the programmed cardiomyocytes and the cardiomyocytes can survive in the culture medium under such condition. In the present invention, a low-sugar-supplemented condition can be achieved by using, for example, RPMI culture medium (sugar -free), and DMEM culture medium (sugar-free) (both from GIBCO).

As used herein, the term "serum component" includes serum itself, components of biologically active agents contained in animal or human serum, and recombinantly or artificially produced components of the biologically active agent. In the present specification, the term "a low-serum -supplemented condition" refers to the condition where the level of the serum or the serum component, or the recombinantly or artificially produced components of the biologically active agent is limited to 0% -10% as compared to the serum level which are supplemented. to the culture medium used for obtaining undifferentiated mesoblast cells is considered to be 100%, and includes, for example, "a serum -free condition". Therefore, an example of "a low-serum -supplemented condition" is the case when 10% serum is supplemented to the culture medium for obtaining the undifferentiated mesoblast cells, the serum concentration in the culture medium is limited to less than 1% for selecting the programmed cardiomyocytes or the cardiomyocytes. The present inventors found that, when the levels of the serum components contained in the culture medium are limited to less than 10% as compared to the levels of the serum components in the culture medium generally used in the art, the non -cardiomyocytes undergo cell death, while the undifferentiated mesoblast cell, the programmed cardiomyocytes and the cardiomyocytes can survive in the culture medium.

In the present invention, the term "a low -nutritional condition" refers to the condition where the levels of every nutritional components contained in the culture mediums which are generally used in the art (such as RPMI culture medium, DMEM culture medium, MEM culture medium, F12 culture medium, and α-MEM culture medium) are limited to less than 10%, as compared to the levels of the nutritional components in the culture medium generally used in the art. In the present invention, it is desirable to limit the levels of the nutritional components to 10%. The present inventors found the when the levels of the nutritional components in the culture medium are limited to 10% as compared to the levels of the nutritional components in the culture medium generally used in the art, the non-cardiomyocytes undergo cell death, while the undifferentiated mesoblast cell, the programmed cardiomyocytes and the cardiomyocytes can survive in the culture medium. Such "a low-nutritional condition" of the culture medium can be prepared by diluting 1 volume of the culture medium generally used in the art (RPMI culture medium, DMEM culture medium, MEM culture medium, F12 culture medium and α-MEM culture medium) using 9 volume of physiological saline (such as Hank's BSS (sugar-free) or PBS).

In the present invention, the term "a low calcium condition" refers to the condition where the calcium concentration contained in the culture medium ranges between 0.3-1.3 mM. The culture media generally used for differentiating into the cardiomyocytes (such as DMEM culture medium, MEM culture medium, and α-MEM culture medium) contain 1.8 mM concentration of calcium in the culture medium. It is known in the art that calcium concentration is kept at around 1.8 mM, throughout the culture period for differentiating into the cardiomyocytes. The present inventors found that when the calcium concentration in the culture medium are limited to 0.3-1.3 mM of calcium concentration, the values of which are significantly lower than the calcium concentration in the culture medium generally used in the art, the non -cardiomyocytes undergo cell death, while the undifferentiated mesoblast cell, the programmed cardiomyocytes and the cardiomyocytes can survive in the culture medium. RPMI culture medium and F12 culture medium (both from GIBCO) can be used as the examples of the culture medium with "a low calcium condition" of the present invention.

In the present invention, the term "a mildly-acidic pH condition" refers to the condition where the pH of the culture medium ranges between pH 6-7. It is known in the art that the pH condition of the culture medium generally used for differentiation induction of the cardiomyocytes (such as RPMI culture medium, DMEM culture medium, MEM culture medium, F12 culture medium, and α-MEM culture medium) is required to be maintained at around pH 7.5 which is the same as the physiological condition. The pH of the basic BSS is adjusted to be around pH 6.5 in the incubator with 5% $CO_2$. The present inventors found that, when the pH of the culture medium is lowered to pH 6.5 which is more acidic than the pH of the culture medium generally used in the art, the non -cardiomyocytes undergo cell death, while the undifferentiated mesoblast cell, the programmed cardiomyocytes and the cardiomyocytes can survive in the culture medium. The culture medium with "a mildly-acidic pH condition " of the present invention can be prepared by adjusting the pH of the culture medium using the Hank's Balanced Salts Solution (Hank's BSS).

In the present invention, the cardiomyocytes can be purified more efficiently by exposing the above mentioned cell mixture to any combination of two or more suitable conditions of the culture medium (i.e., the physiological resistance -based selection method).

The present inventors found that, when the culture medium is deprived of the sugars, the non-cardiomyocytes underwent cell death within the embryoid bodies derived from the embryonic stem cells. The present inventors further studied an alternative substrate which can preferentially provide the cardiomyocytes with an energy other than the sugars, for the purpose of further improving the selectivity of the undifferentiated mesoblast cell, the programmed cardiomyocytes and the cardiomyocytes contained in the embryoid bodies.

As a result, the present inventors found that it is effective to supplement to the culture medium a lactic acid (Lactate, 0.1-5 mM), a combination of an aspartic acid (20-100 mg/L) and a glutamic acid (20-100 mg/L), or a pyruvic acid (0.5-5 mM), or any combinations thereof in place of the sugars. Based on these findings, it is considered that such sugar substitutes can specifically provide the cardiomyocytes with necessary nutrients.

The selection method described above is referred to as "metabolism-based selection method" since the method uses metabolic capability of the cardiomyocytes to select the cardiomyocytes. The metabolism-based selection method of the invention is characterized by culturing the cell mixture containing the cardiomyocytes under a lactic acid-supplemented condition, an aspartic acid/glutamic acid-supplemented condition, or a pyruvic acid-supplemented condition.

In the present invention, the two types of methods for selecting the cardiomyocytes (i.e., the physiological resistance-based selection method and the metabolism-based selection method) can be used in combination to purify the cardiomyocytes at a high degree of purity. Also, the above methods are repeatedly carried out to attain a further high degree of purification.

The cell mixture containing the undifferentiated mesoblast cell, the programmed cardiomyocytes and the cardiomyocytes which are used in the present invention as an origin of the cardiomyocytes can also be prepared from stem cells or fetuses. In this context, the term "stem cells" includes, but not limited to, totipotent cells which can differentiate into any types of cells (such as embryonic stem cells) and pluripotent cells which can differentiate into multiple particular types of cells (such as adult stem cells derived from the bone marrow).

It is believed that, in the course of preparation of the cardiomyocytes from the embryonic stem cells, as differentiation progresses, the embryonic stem cells differentiate into the undifferentiated mesoblast, and then subsequently change into the programmed cardiomyocytes, and finally form the cardiomyocytes. Here, the "undifferentiated mesoblast cell" refers to the cells which express the Brachyury protein (a specific marker for the undifferentiated mesoblast cells). Meanwhile, the "programmed cardiomyocytes" refers to the cells which express the undifferentiated mesoblast cell-specific proteins such as the Brachyury protein but do not express the cardiomyocyte specific proteins such as Nkx2.5 and Actinin. The programmed cardiomyocytes has an ability to exclusively differentiate into the cardiomyocytes without a need to supplement of any additional substances to the culture medium. The "cardiomyocytes" refers to autonomously pulsating cells when the cells are viable and also cells expressing some markers such as Nkx2.5, GATA4, and Actinin, which can be detected after fixation.

For example, when the mouse embryonic stem cells are used as an origin of the cardiomyocytes, the cell population which can survive under these culture conditions can be selected as a cell population consisting of the programmed cardiomyocytes or the cardiomyocytes from cells consisting of the embryoid bodies by the following steps: inducing differentiation of the mouse embryonic stem cells by eliminating LIF from the culture medium, then incubating for 4-7 days the mouse embryonic stem cells to generate embryoid bodies, and culturing the embryoid bodies under the physiological resistance-based selection method and/or the metabolism-based selection method to select the viable cell population as the programmed cardiomyocytes or the cardiomyocytes.

By way of example, after 5 days from the start of the differentiation induction, cells were selected for additional 24 hours under a low-sugar-supplemented condition and any one of or any combinations of four types of the conditions (i.e., a low-serum-supplemented condition, a low-nutritional condition, a low calcium condition, and a mildly-acidic pH condition). Though the selected cells were those with no pulsating ability, the cell population with no pulsating ability were immunostained using an antibody against the Brachyury, the marker of the undifferentiated mesoblast cell, resulting in the Brachyury positive images in almost all cells. This means that the present method is a method for effectively selecting the undifferentiated mesoblast cells.

Further, the Brachyury positive cells were immunostained it an antibody against the Nkx2.5 (which is a presently-known earliest developmental homeotic protein marker specific for the cardiomyocytes), resulting in the negative images in almost all cells. Nevertheless, continued culture of the cells resulted in differentiation of about 80-90% of the cells into the cardiomyocytes. Therefore, it is considered that the undifferentiated mesoblast cells selected in the method above are unknown but the most primitive programmed cardiomyocytes.

By way of another example, to select the cardiomyocytes, the embryoid bodies derived from the embryonic stem cells after 4-6 days from the start of differentiation induction can be cultured for about 3 days in the serum-free culture medium prepared by mixing MEM (Minimum Essential Medium) [Hank's BSS] (Invitrogen) and α-MEM (SIGMA) at the ratio of MEM [Hank's BSS]: α-MEM=9:1-1:9, supplemented with ITS [insulin (10 mg/L), transferrin (5.5 mg/L), and sodium selenite (6.7 mg/L)] (GIBCO) (in this case, the calcium concentration was about 1.3 mM). This culture medium condition corresponds to a low-serum -supplemented condition, a low calcium condition and a mildly -acidic pH condition. The thus prepared programmed cardiomyocytes can be continuously cultured in the same culture medium to differentiate into the cardiomyocytes. When the above manipulation of the cell mixture is conducted after 5 days from the start of differentiation induction, especially after induction of the autonomously pulsating cardiomyocytes, it is possible to efficiently select the cardiomyocyte by simply culturing in MEM [Hank's BSS] under a low-serum -supplemented condition and a mildly-acidic pH condition. The thus prepared cardiomyocytes can be continuously cultured in the mixed culture medium of MEM and α-MEM to differentiate into atrial muscle and ventricle muscle.

By way of further example, the embryoid bodies derived from the embryonic stem cells were washed using a sugar-free medium such as Hank's BSS (GIBCO) to thoroughly eliminate sugars and then cultured for 3-7 days in the culture medium (Hank's BSS [sugar-free]/DMEM [sugar-free]=9:1) under a low-serum-supplemented condition, a low-nutritional condition (such as those prepared by 10 times diluting a commercially available culture medium with isotonic buffer solution), a mildly-acidic pH condition, and a low calcium condition, which were supplemented with 1 mM of a lactic acid (a lactic acid-supplemented condition), 20 mg/L of an aspartic acid and 20 mg/L of glutamic acid (an aspartic acid/ glutamic acid-supplemented condition), or 1 mM of a pyruvic acid (a pyruvic acid-supplemented condition). As a result, it is possible to efficiently select the cardiomyocyte by the method above.

In an attempt to prepare the cardiomyocytes using the adult stem cells derived from bone marrow, the methods described above are also applicable to select the cardiomyocytes from the cell mixture of the adult stem cells. Here, the cardiomyocytes derived from the mouse bone marrow were induced using the cells and the method as described in WO01/048151 (PCT/JP00/09323). That is to say, CMG cells are cultured in IMDM (Iscove's Modified Dulbecco's Medium) (GIBCO) supplemented with 20% of fetal bovine serum (regarding the method for establishing CMG cells, see, J. Clin. Invest., 1999, Vol. 103, p697-705), cultured for additional 24 hours in a culture medium supplemented with a final concentration of 3 μmol/l of 5-azacytidine (SIGMA), then cultured for 2-3 weeks in the culture medium above without 5-azacytidine. As a result, this selection method enables differentiation induction of the cells into autonomously pulsating cardiomyocytes. It is possible to obtain the cardiomyocytes by further culturing the cell mixture containing the autonomously pulsating cardiomyocytes under the physiological resistance-based selection method and/or the metabolism-based selection method.

Further, in the course of preparation of the cardiomyocytes from the mouse fetuses, the cardiomyocytes can be selected and purified from the 7th day of embryonic life (the time point when the cardiomyocytes first appear; the time point corresponds to day 16 after the fertilization in the case of human) by the following procedure: i.e., aseptically removing mouse fetuses, washing them using Hank's BSS [sugar -free] four times, pipetteing several times using 10 ml pipette to disperse fetuses to separate cell masses, culturing the cell masses under the physiological resistance-based selection method and/or the metabolism-based selection method, and selecting the cardiomyocytes.

In this way, in the present invention, the cell mixture containing the undifferentiated mesoblast cell, the programmed cardiomyocytes and the cardiomyocytes used as an origin of the cardiomyocytes is cultured under the physiological resistance-based selection method and/or the metabolism-based selection method to acquire masses of the cardiomyocytes which are formed by adhering the cardiomyocytes with each other. However, since the thus prepared masses of the cardiomyocytes are covered by a layer of the dead non-cardiomyocytes, it is necessary to eliminate the dead non-cardiomyocyte layer from the masses before transplanting the masses of the cardiomyocytes. Regarding this matter, the present inventors further studied as described below.

The present inventors further found that, when cell masses are treated with a general cell dispersion method (such as those using random proteolytic enzymes such as Trypsin or ion chelating agents such as EDTA), the dispersed cells significantly lose viability of the cells. Therefore, there need a novel method for efficiently eliminating the dead cells adhered on the surface of the embryoid bodies while maintaining the masses of the cardiomyocytes.

It is generally considered that cell-cell conjugation is achieved by the binding through the extracellular matrix (such as collagen, fibronectin, and elastin) or by direct binding between the membrane proteins. The present inventors found that digestion of the masses of the cardiomyocytes using collagenase or elastase (which have a high specificity for the matrix proteins) could efficiently eliminate the dead non-cardiomyocytes adhered on the surface of the cell masses of the cardiomyocytes while maintaining the shapes of the masses without being dispersed into separate cells. From the results, cell-cell adhesion between the cardiomyocytes is formed by the direct binding through N-cadherin or connexin.

In the present invention, it is possible to efficiently eliminate the dead cells by, for example, shaking the embryoid bodies in the presence of 0.01-0.1% of type III collagenase (Wartington) for 20 minutes in the water bath of 37° C., separating the dead cells from the cardiomyocytes, repeating centrifugation and supernatant replacement four times to completely wash out the collagenase, and obtaining the final product.

However, even after collagenase treatment, the thus obtained aggregates may possibly and undesirably contain the dead cells of the non-cardiomyocytes. The longer the metabolism-based selection is conducted, the more frequently the aggregates containing dead cells may appear. Examining the density of such aggregates containing dead cells, the present inventors found that the density and the specific gravity of the dead cells is higher than those of the living cells and also found that the living cells can be separated from the dead cells using the suitable density gradient centrifugation method. An agent used for separating viable cells from dead cells through the density gradient centrifugation method includes, but not limited to, Percoll™ (Pharmacia), Ficoll™ (Pharmacia), Optiprep (GIBCO).

EXAMPLES

Example 1

Formation of Cardiomyocyte Selective Aggregates by Culturing the Mouse Embryonic Stem Cells Under a Low-Serum-Supplemented Condition or a Serum-Free Condition This Example aims at studying the effect of serum depletion on the cell masses containing the cardiomyocytes (embryoid bodies), more specifically the effect of the serum depletion on selection of the cardiomyocytes from the cell masses (the embryoid bodies), by culturing the cell masses (the embryoid bodies) in the serum-free culture medium.

The mouse embryonic stem cells (the name of the cell line is EB3, Nat, Genet., 2000; 24: 372-376) were kindly provided by Dr. Hitoshi Niwa of RIKEN, Japan. The mouse embryonic stem cells are cultured for total 7 days using a method similar to the existing method (Differentiation 2001, 68, p31-43), i.e., 75 ES cells per one EB were cultured as the cell masses for total 7 days in the culture medium [(α-MEM (Minimum Essential Medium) (SIGMA), 10% FBS (EQUITEC BIO), 100 units/ml penicillin, 50 μg/ml streptomycin (GIBCO)] using the hanging drop method, After differentiating into the cell masses (the embryoid bodies) containing the cardiomyocytes using the above method, the embryoid bodies were cultured with being adhered on a culture dish using the culture medium described above for 3-5 days at 37° C. in 5% $CO_2$. The method described above is the conventional cardiomyocyte differentiation method. FIG. 1 shows appearance of the cell masses obtained under the conventional method above. Here, FIG. 1A shows a microscopic appearance of the embryoid body; FIG. 1B shows the outline of existence region of the cardiomyocytes in the embryoid body which was detected by specific fluorescent immunostaining using the anti-Actinin antibody (SIGMA); and FIG. 1C shows the outline of the cardiomyocyte existence region in the embryoid body which was identified by the fluorescent immunostaining, and was delineated on the phase-contrast microscopic image of FIG. 1A. As shown in the scheme of a mode of existence of the cardiomyocytes within an adhered embryoid body (FIG. 1D), the cardiomyocytes were surrounded by other cells and were hard to be separated and purified from the embryoid body.

On the other hand, the mouse embryonic stem cells were differentiated into the cell masses (the embryoid bodies) containing the cardiomyocytes under the same condition, were cultured for 5 days with being adhered on a culture dish, and then cultured for additional 3 days in the serum-free culture medium for the embryoid bodies containing the cardiomyocytes.

Figure 2:
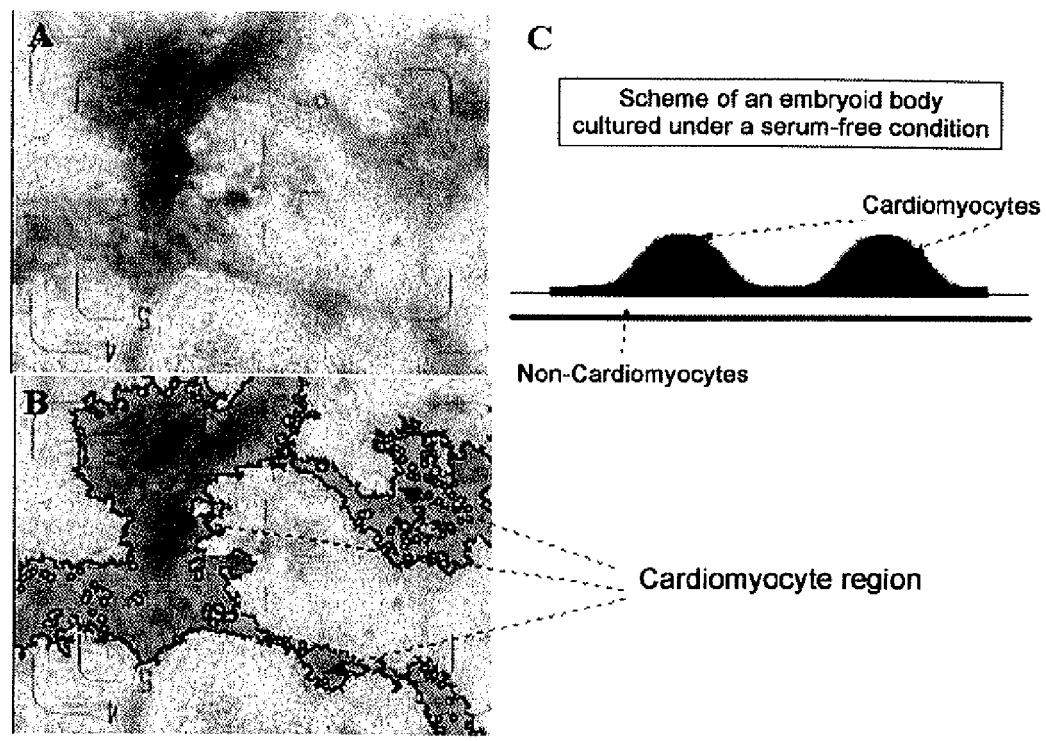
FIG. 2 shows a mode of presentation of the cardiomyocytes within the adhered embryoid bodies which were cultured under a serum-free condition.

The results are shown in FIG. 2. Here, FIG. 2A shows microscopic images of the adhered embryoid bodies subjected to the selective culture under the above condition, and FIG. 2B shows the outline of the autonomously pulsating cardiomyocyte region within the embryoid bodies which was identified by the video analysis. As shown in the scheme of a mode of existence of the cardiomyocytes within the embryoid bodies after the selective culture (FIG. 2C), the cell population of the cardiomyocytes exist at the surface region of the embryoid bodies, where the cardiomyocytes were found to be aggregated with each other.

Example 2

Formation of the Programmed Cardiomyocytes Selective Aggregates and Formation of Aggregates Containing the Cardiomyocytes at a High Rate by Culturing the Mouse Embryonic Stem Cells Under a Low-Serum- Supplemented Condition or a Serum-Free Condition.

This Example aims at studying the effect of serum depletion on the cell masses (the embryoid bodies) containing the programmed cardiomyocytes, more specifically the effect of serum depletion on selection of the programmed cardiomyocytes form the cell masses (the embryoid bodies), by culturing the cell masses (the embryoid bodies) containing the programmed cardiomyocytes in the serum-free culture medium.

Figure 3:
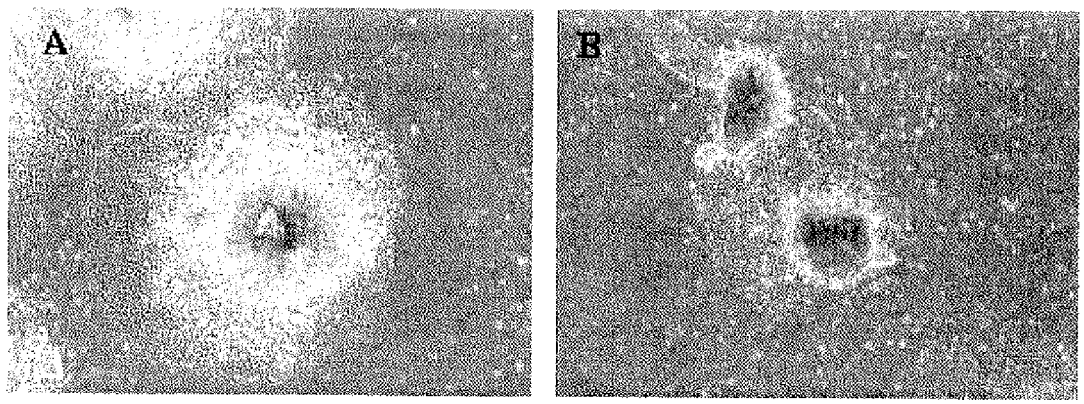
FIG. 3 shows a successful selection of the programmed cardiomyocytes under a serum-free condition.

The mouse embryonic stem cells were cultured for 5 days using a standard method described in Example 1 in the culture medium [α-MEM (SIGMA), 10% FBS (EQUITEC BIO), penicillin/streptomycin (GIBCO)], i.e., 75 ES cells per one EB were cultured as the cell masses in the culture medium above using the hanging drop method for 5 days at 37° C. in 5% $CO_2$ to form embryoid bodies. Autonomously pulsating cells were observed in the embryoid bodies on 7 days from the start of the differentiation culture of the cells using the existing culture method (as defined in Example 1). Then, after 5 days from the start of the differentiation culture of the cells, the stage when any autonomously pulsating cardiomyocytes have not yet observed, the cells were cultured under the serum-free condition for an additional 1 day (24 hours) (the same results are produced in both situations when the culture was started on 4 days or 6 days from the start of the differentiation culture). FIG. 3A shows morphological appearance of the embryoid bodies which were cultured in the normal serum-supplemented condition for 6 days, while FIG. 3B shows morphological appearance of the embryoid bodies at around the same stage as FIG. 3A, which were cultured under a serum-free condition for an additional 1 day (24 hours) at the 5th day from the start of the culture.

When the cell masses shown in FIG. 3B which were prepared by culturing under a serum-free condition for an additional 1 day (24 hours) at the 5th day from the start of the culture (i.e., by the following steps: transferring the culture medium containing the embryoid bodies to a centrifuging tube followed by spontaneous precipitation, removing the supernatant, washing once using serum-free culture medium [α-MEM (SIGMA), insulin/transferrin/selenium (GIBCO), and penicillin/streptomycin (GIBCO)], and then substituting with the same culture medium.) were further cultured for additional 1-4 days, the cultured cells are differentiated into the cell masses containing autonomously pulsating cardiomyocytes at a high rate. Therefore, the results demonstrate that the cell masses containing the programmed cardiomyocytes, which are not autonomously pulsating but are programmed to differentiate into the cardiomyocytes in the future, at a high rate can be formed, by culturing the mouse embryonic is cells under a serum-free condition for an additional 1 day (24 hours) at the 5th day from the start of the culture.

Example 3

Selective Inhibition of Differentiation/Growth of Cells Other Than the Cardiomyocytes by Culturing the Mouse Embryonic Stem Cells Under a Low Calcium Culture Medium Condition This Example aims at studying the effect of lowered calcium concentration on the cell masses (the embryoid bodies) containing the cardiomyocytes, more specifically the effect of the lowered calcium concentration on selection of the cardiomyocytes from the cell masses (the embryoid bodies), by culturing the cell masses (the embryoid bodies) in the culture medium under the lowered calcium concentration.

The mouse embryonic stem cells were cultured for total 7 days using a standard method described in Example 1 in the culture medium [α-MEM (SIGMA), 10% FBS (EQUITEC BIO), penicillin/streptomycin (GIBCO)], i.e., 75 ES cells per one EB were cultured as the cell masses in the culture medium using the hanging drop method for total 7 days to form embryoid bodies, which were then differentiated into the cell masses (the embryoid bodies) containing the cardiomyocytes. The calcium concentration in the culture medium for the cardiomyocyte differentiation was 1.8 mM. In the case of this culture method, the content of the cardiomyocytes was about 10%, while other cells were made of the undifferentiated cells, the neuronal cells, and the epithelial cells.

Figure 4:
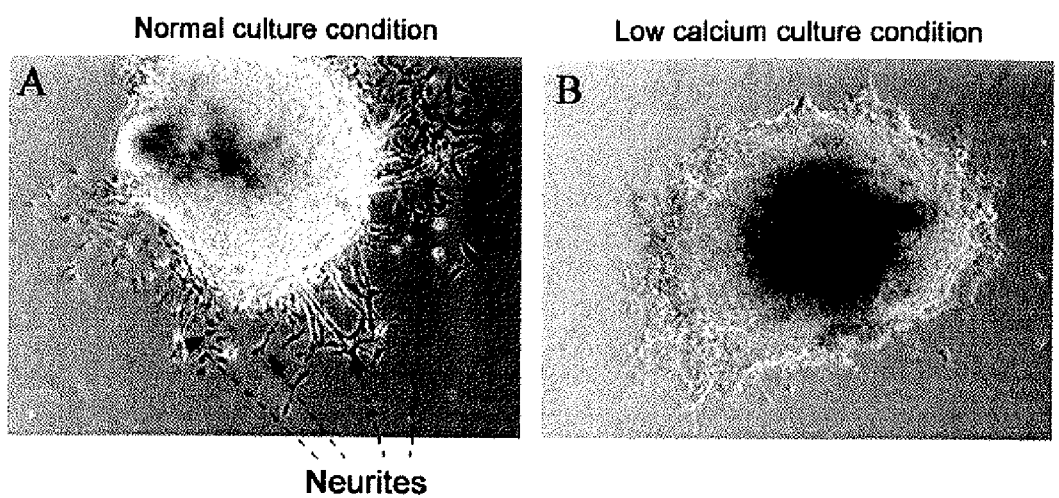
FIG. 4 shows an effect of low calcium condition.

On the other hand, in this Example, 75 mouse ES cells per one EB were cultured as the cell masses for 5 days in the culture medium [α-MEM (SIGMA), 10% FBS (EQUITEC BIO), penicillin/streptomycin (GIBCO)] to form the embryoid bodies using the hanging drop method, which were then adhered on the culture plate, and further cultured in the same culture medium for an additional 1 day (24 hours). Then, 6 days after the start of the differentiation culture, i.e., 1 day (24 hours) after adhering the embryoid bodies on the plate, in the control group, the embryoid bodies were cultured in RPMI culture medium (calcium concentration of 1.8 mM) supplemented with 10% FBS by day 8 of culture (FIG. 4A), while in the experimental group, the embryoid bodies were cultured in RPMI culture medium (calcium concentration of 0.4 mM; GIBCO) supplemented with 10% FBS (FIG. 4B). As a result, in comparison with the untreated embryoid bodies, in the case of the embryoid bodies treated with a low calcium condition, growth of flat-shaped cells was suppressed around the periphery of the embryoid bodies, or differentiation of the embryoid bodies into the neuronal cells was inhibited (FIG. 4B).

Example 4

Selection of the Programmed Cardiomyocytes From the Mouse Embryonic Stem Cells Under a Serum-Free/a Mildly-Acidic pH Condition This Example aims at studying the complexed effect of serum depletion and a mildly-acidic pH condition on the cell masses (the embryoid bodies) containing the programmed cardiomyocytes, more specifically the complexed effect of serum depletion and a mildly-acidic pH on selection of the programmed cardiomyocytes from the cell masses (the embryoid bodies), by culturing the cell masses (the embryoid bodies) in culture medium under serum-free and a mildly-acidic pH condition.

In this Example, 75 mouse ES cells per one EB were cultured as the cell masses for 5 days from the start of the differentiation in the culture medium [α-MEM (SIGMA), 10% FBS (EQUITEC BIO), penicillin/streptomycin (GIBCO)] using the hanging drop method to form embryoid bodies, which were then differentiated into the cell masses (the embryoid bodies) containing the programmed cardiomyocytes. In this Example, 5 days after the start of the differentiation culture of the cells, the stage when any autonomously pulsating cardiomyocytes have not yet observed, the cells were further cultured in MEM (Minimum Essential Medium) (GIBCO) supplemented with insulin/transferrin/selenium (GIBCO) for an additional 1 day (24 hours) culture medium (the same results are produced in both situations when the culture was started on 4 days or 6 days from the start of the differentiation culture). Since the pH condition of this culture medium is adjusted to heat around pH 6.5 under 5% $CO_2$ condition, the cells were cultured in the mildly-acidified culture medium under 5% $CO_2$ condition.

Figure 5:
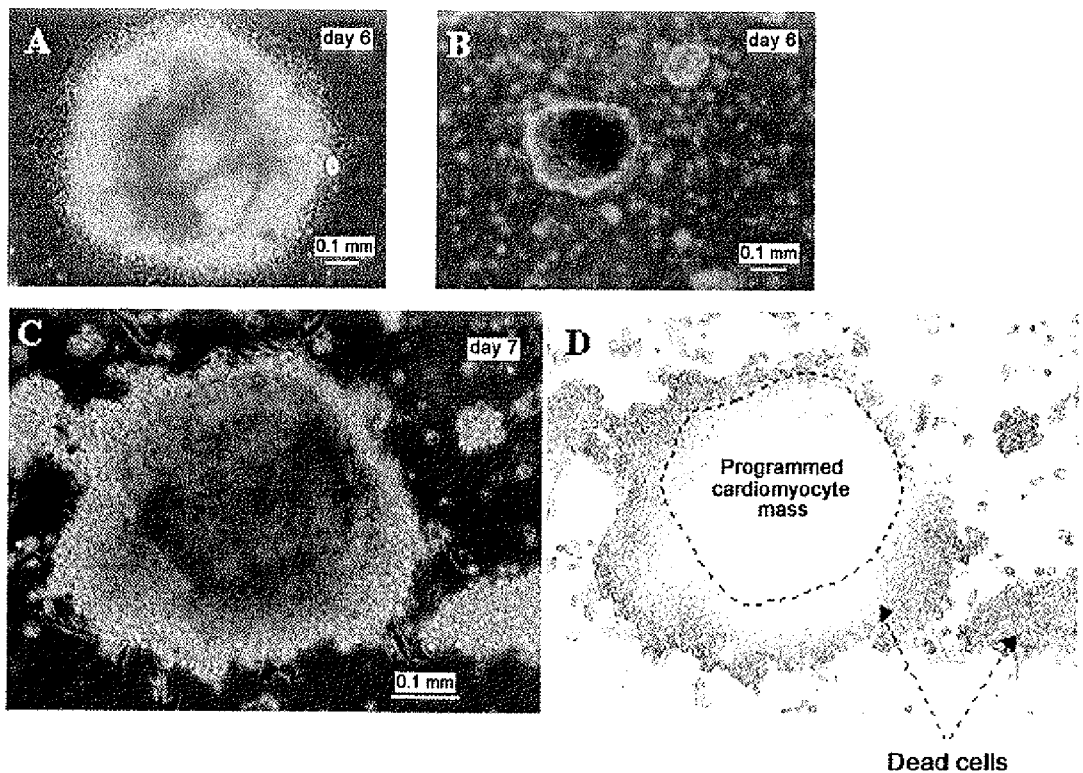
FIG. 5 shows a successful selection of the programmed cardiomyocytes within the mass of the embryonic stem cells under a serum-free/mildly acidic pH condition.

The culture resulted in forming the cell masses containing the programmed cardiomyocytes without autonomously pulsating at a high rate. FIG. 5A shows morphological appearance of the adhered embryoid body which was cultured in the normal serum-supplemented condition, FIG. 5B shows morphological appearance of the embryoid body which was cultured for 1 day (24 hours) under a serum-free condition, and FIG. 5C shows morphological appearance of the embryoid body which was cultured for 2 days (48 hours) under a serum-free condition, respectively. Under the condition shown in FIG. 5C, the cells adjacent to the surface of the embryoid body are selectively underwent cell death, while the cells at the central part the embryoid body did not undergo cell death (FIG. 5), FIG. 5D shows the outline of the region of the programmed cardiomyocytes based on the analysis shown in FIG. 5C, and also show the dead cells indicated by arrows.

The inventors obtained two types of the cell masses in this Example: one type of the cell masses was selected by culturing the embryoid bodies after 5 days from the formation thereof for additional 24 hours under a serum-free/a mildly-acidic pH condition; the other type of the cell masses was selected by further culturing the cell masses obtained above for additional 3 days (72 hours). Frozen sections of these cell masses were prepared to immunostain using an anti-Brachyury antibody (Santacruz) against the Brachyury protein (which is an undifferentiated mesoblast cell marker) (FIGS. 6A-6D). As a result, the proportion of the Brachyury -positive cells cultured for 24 hours under a serum -free/ mildly-acidic pH condition (FIGS. 6B and 6D) was significantly higher in comparison with that of the Brachyury -positive cells cultured for 24 hours in the culture medium containing serum-supplemented and at the neutral pH condition (FIGS. 6A and 6C). The cell masses cultured for additional 3 days were immunostained using an antibody against Nkx2.5 (anti-Nkx2.5 antibody (Santacruz)) (FIGS. 6E-6N). The marker Nkx2.5 is believed as an earliest developmental marker expressed in the cardiomyocytes and is known to be continuously expressed in the cardiomyocytes differentiated. FIGS. 6E-H show morphological appearance of the embryoid bodies (EB) which were prepared by culturing for 24 hours in the culture medium containing serum and at the neutral pH, followed by culturing for additional 3 days in the same culture medium. It is shown that a part of cells inside the EB was differentiated into the cardiomyocytes under these culture conditions. Further, the proportion of the cells differentiated into the cardiomyocytes was similar to that of the Brachyury positive cells (FIGS. 6A and 6C). On the other hand, in the case of the EBs which were cultured for 24 hours under a serum-free/a mildly-acidic pH condition (shown in FIGS. 6I-N), the proportion of the cells differentiated into the cardiomyocytes accounted for as much as 80% of the total number of the cells, which was also similar to that of the Brachyury positive cells (FIGS. 6B and 6D).

Figures 1, 6:
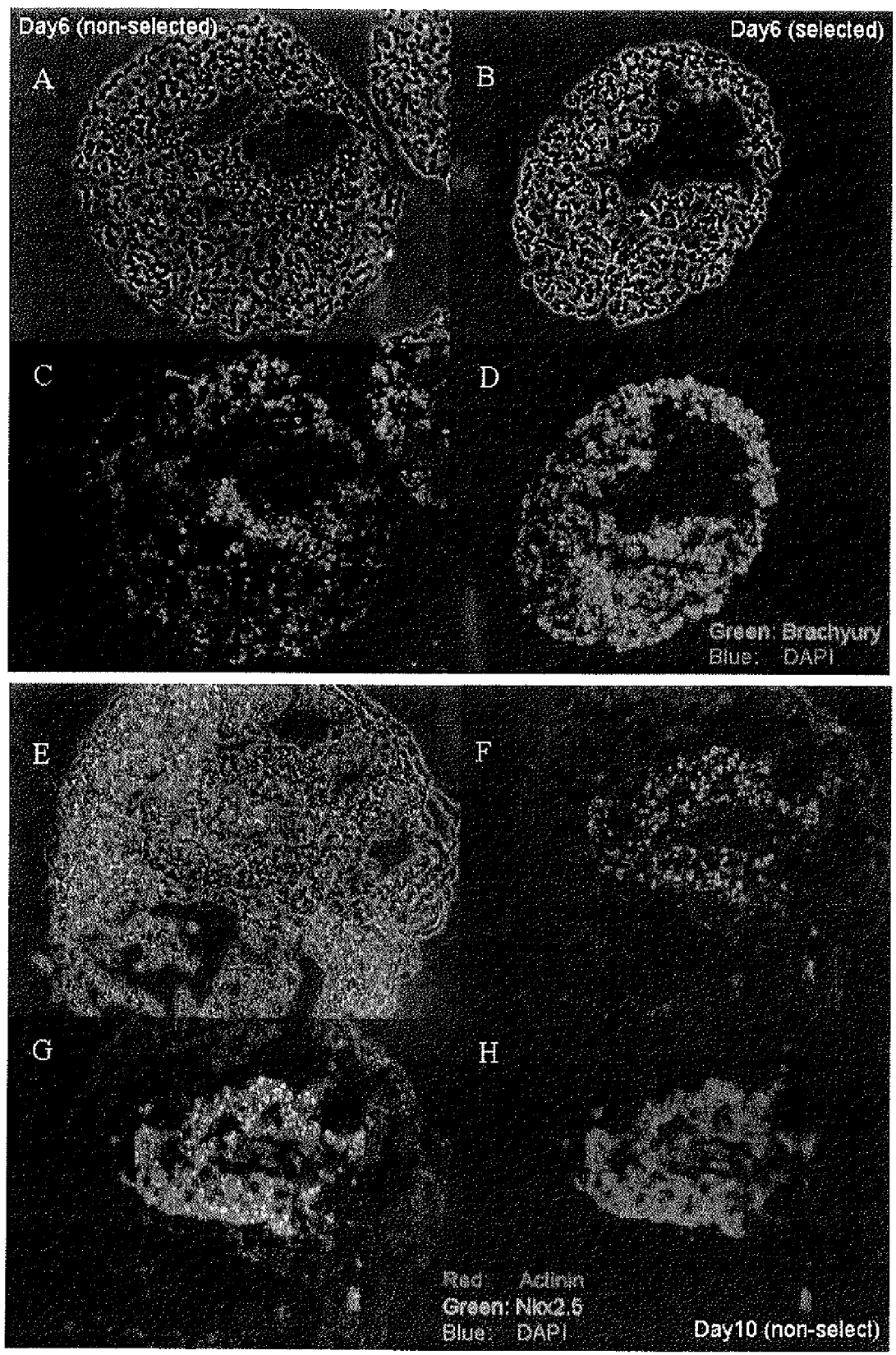
Figures 2, 6:
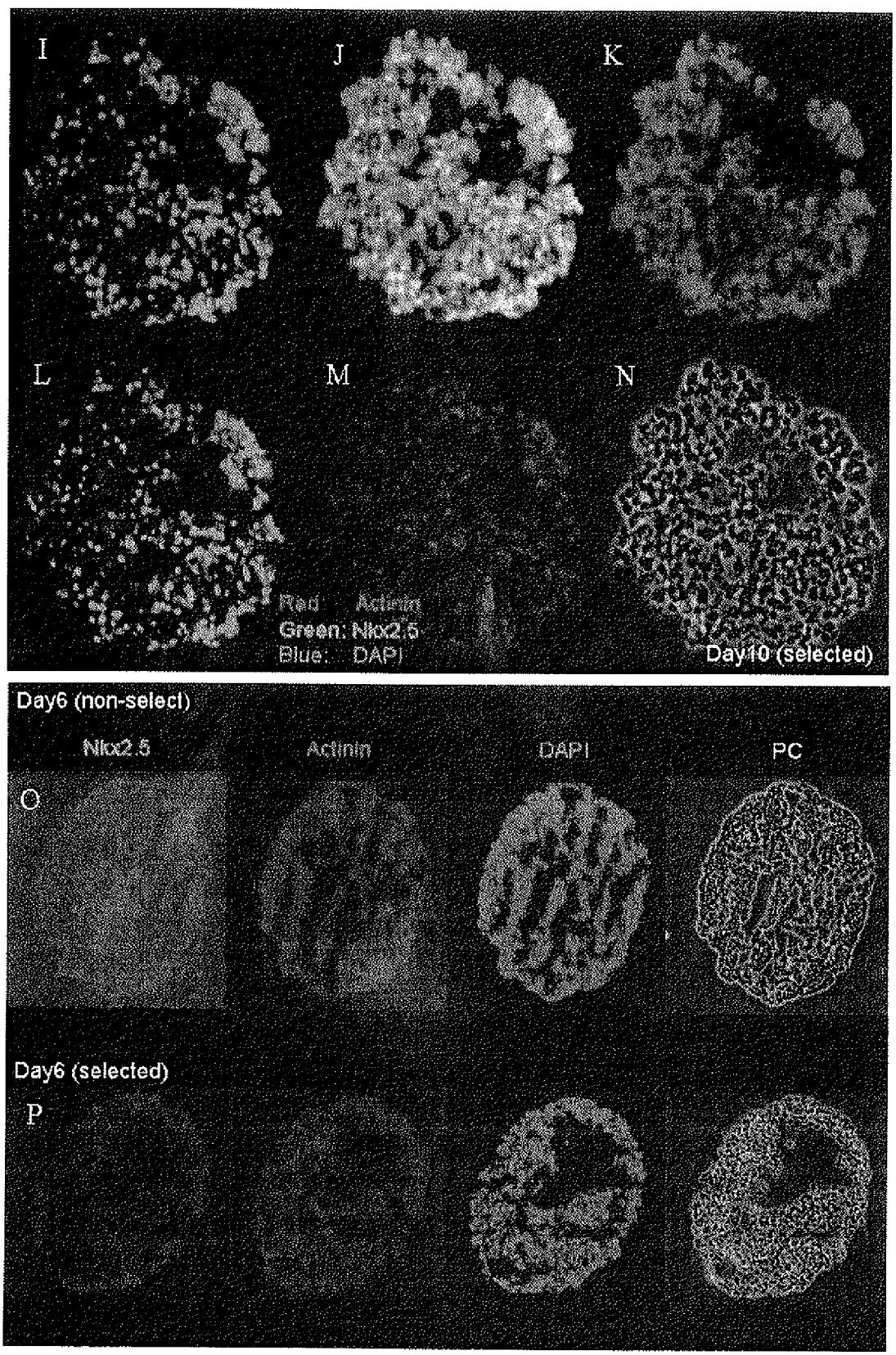

The cells selected by the 5 days+1 day (24 hours) procedure were positive for the anti-Brachyury antibody but were negative for the anti-Nkx2.5 antibody (FIGS. 6, lines O and P). While, the cell masses selected by the 5 days+1 day (24 hours)+3 days procedure were negative for the anti-Brachyury antibody, but were positive for the anti-Nkx2.5 antibody.

Thus, the all masses containing the autonomously pulsating cardiomyocytes at high rate were differentiated by culturing these cell masses for additional 1-4 days. Therefore, cells selected by the 5 days+1 day (24 hours) procedure were confirmed to be the programmed cardiomyocytes.

Example 5

Selection of the Cardiomyocytes From the Mouse Embryonic Stem Cells by Culturing Under a Serum-Free/a Mildly-Acidic pH Condition This Example aims at studying the complexed effect of a serum depletion and a mildly-acidic pH condition on the cell masses (the embryoid bodies) containing the cardiomyocytes, more specifically the complexed effect of a serum depletion and a mildly-acidic pH condition on selection of the cardiomyocytes from the cell masses (the embryoid bodies), by culturing the cell masses (the embryoid bodies) in the serum-free culture medium under a mildly-acidic pH condition.

Figure 7:
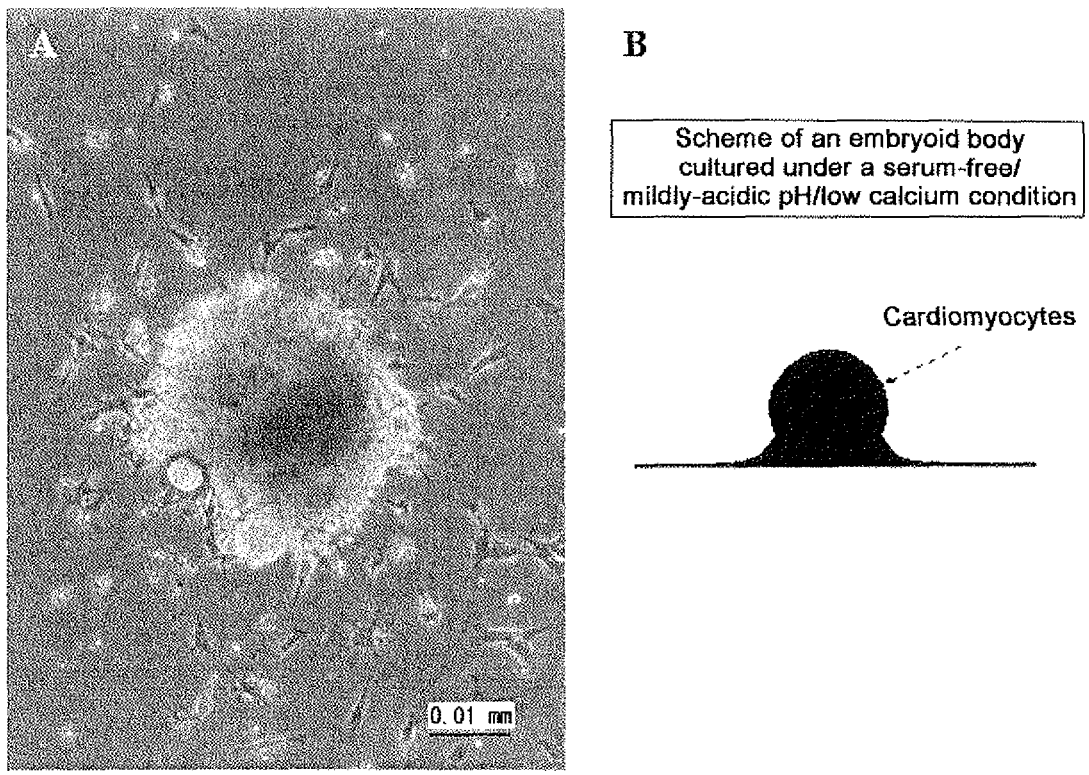
FIG. 7 shows a mass of cardiomyocytes which is selected by culturing embryonic stem cells under a serum-free/mildly-acidic pH condition.

In this Example, 75 mouse ES cells per one EB were cultured as the cell masses for 5 days from the start of the differentiation in the culture medium [α-MEM (SIGMA), 10% FBS (EQUITEC BIO), penicillin/streptomycin (GIBCO)] using the hanging drop method to form embryoid bodies, which were then differentiated into the cell masses (the embryoid bodies) containing the programmed cardiomyocytes. In this Example, after 5 days from the start of the differentiation culture of the cells, the stage when any autonomously pulsating cardiomyocytes have not at observed, the cells were further cultured in the serum-free MEM culture medium (GIBCO) supplemented with insulin/transferrin/selenium (GIBCO) for additional 2 days (the same results are produced in both situations when the culture was started on 4 days or 6 days from the start of the differentiation culture). These thus obtained cell masses of the programmed cardiomyocytes were further cultured for additional 2 days to differentiate into the cardiomyocytes. FIG. 7A shows a microscopic image of the thus prepared mass of the cardiomyocytes, and FIG. 7B shows a scheme of the lateral appearance of the embryoid body of FIG. 7A.

Under the condition above, the cells other than the cardiomyocytes selectively underwent cell death, while the cardiomyocytes exhibit strong and autonomous pulsating without undergoing cell death. As a result, the cell masses containing a high proportion of the cardiomyocytes are generated in this Example (FIGS. 7A and FIG. 7B).

Example 6

Selection of the Cardiomyocytes by Culturing Under a Sugar-Free/a Serum-Free and a Lactic Acid -Supplemented Condition and Preparation of the Cardiomyocytes This Example aims at studying the complexed effect of serum depletion and sugar depletion on the cell masses (the embryoid bodies) containing the cardiomyocytes, more specifically the complexed effect of serum depletion and sugar depletion on selection of the cardiomyocytes from the cell masses (the embryoid bodies), by culturing the cell masses (the embryoid bodies) in the sugar-free and serum-free culture medium.

In this Example, 75 mouse ES cells per one EB as the cell masses were cultured for total 7 days in the culture medium [α-MEM (SIGMA), 10% FBS (EQUITEC BIO), penicillin/streptomycin (GIBCO)] using the hanging drop method to form embryoid bodies, which were then differentiated into the cell masses the embryoid bodies) containing the cardiomyocytes. The embryoid bodies cultured for 10 days from the start of differentiation were washed 4-5 times using D-MEM (Dulbecco's Modified Eagle Medium) (sugar-free) culture medium (GIBCO) to thoroughly eliminate sugars in the culture medium and then were cultured for 7 days in D-MEM culture medium (GIBCO) supplemented with a lactic acid at a final concentration of 1 mM (it is necessary to visually measure the viability of the autonomously pulsating cardiomyocytes and other cells in the multiple times of experiments and to adjust the culture period between 5-10 days on the basis of the viability). Since the in vivo concentration of a lactic acid increases to about 4 mM under the physiological condition, the concentration of a lactic acid of "1 mM" used in the method of this Example falls within the physiological range.

Figure 8:
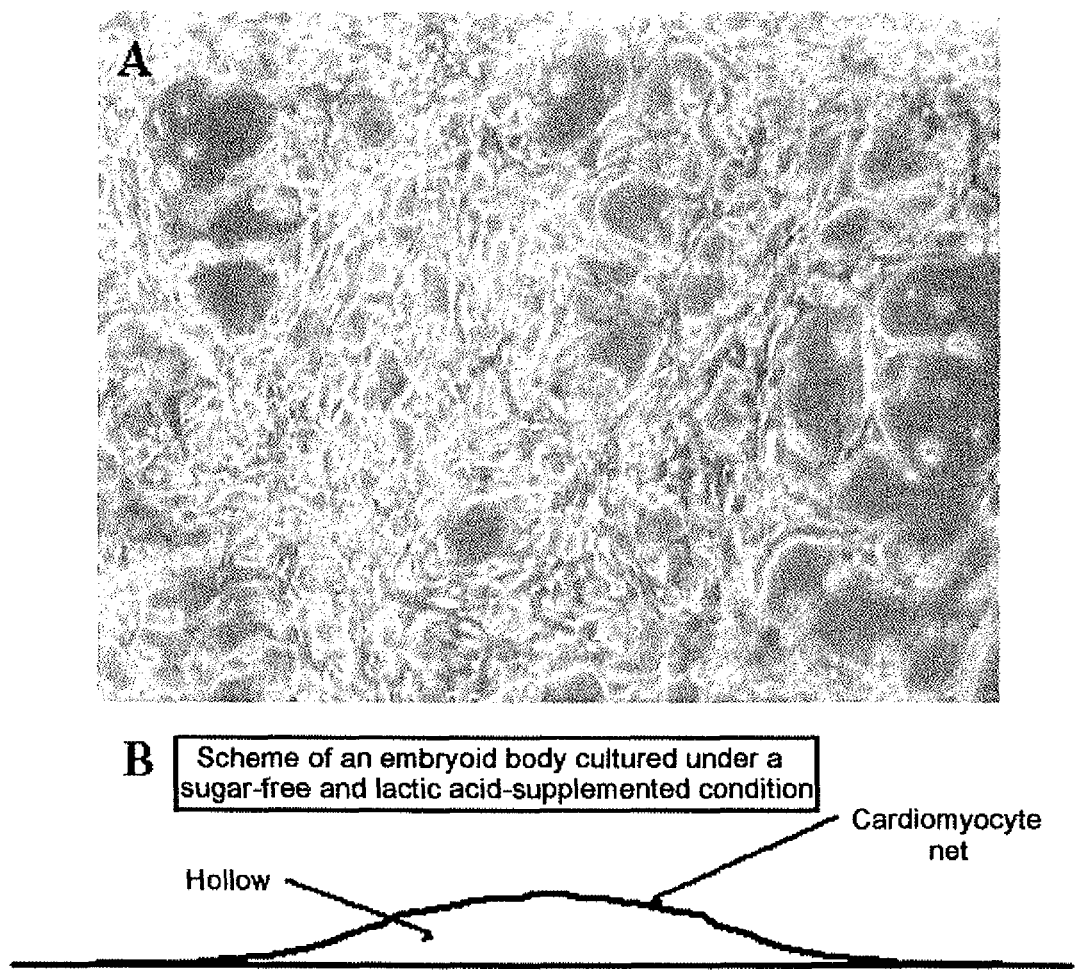
FIG. 8 shows selection of cardiomyocytes by culturing the cells under a sugar-free, a serum free and a lactic acid-supplemented condition.

As shown in FIG. 8, a domy shaped cellular net consisting of the viable cardiomyocyte was formed. That is to say, FIG. 8A shows an image of a net-like structure formed, by the selected cardiomyocytes, and FIG. 8B shows a scheme of the lateral view of the embryoid body of FIG. 8A.

Example 7

Elimination of Dead Cells Adhered to Masses of the Cardiomyocytes

Since the cell masses prepared in Example 6 were adhered by dead cells or extracellular matrix proteins, it is necessary to remove dead cells or extracellular matrix proteins from the masses of the cardiomyocytes to purify the masses. However, it was shown by preliminary study that an enzyme causing non-specific proteolysis (such as Trypsin) significantly decrease the viability of the cardiomyocytes.

So, this Example aims at studying a condition for selectively removing the dead cells or the extracellular matrix protein from the masses containing the cardiomyocytes.

The cell masses prepared in Example 6 (shown in FIG. 8) were treated with 0.01-0.1% of collagenase, which selectively digests the collagen, one of the extracellular matrix proteins, at 37° C. for 20 minutes, After treatment with only collagenase, the cell masses were washed with an isotonic solution having a physiological osmotic pressure. At this stage, since the cardiomyocytes form the cell masses (no less than 40 μm in diameter), the cell masses were washed by solution exchange through the commercially available membrane having pores of 40 μm in diameter, and then the cells other than the cardiomyocytes dispersed were selectively removed. The washing step was repeated 4-5 times. The collected cell masses were cultured and then were immunostained using an anti-sarcomere-Actinin antibody (SIGMA) as an indicator of the cardiomyocytes (Red: [staining of the cross-striated fiber in cytoplasm], Blue: [staining of the nucleus with DAPI (Molecular probe)]).

Figure 9:
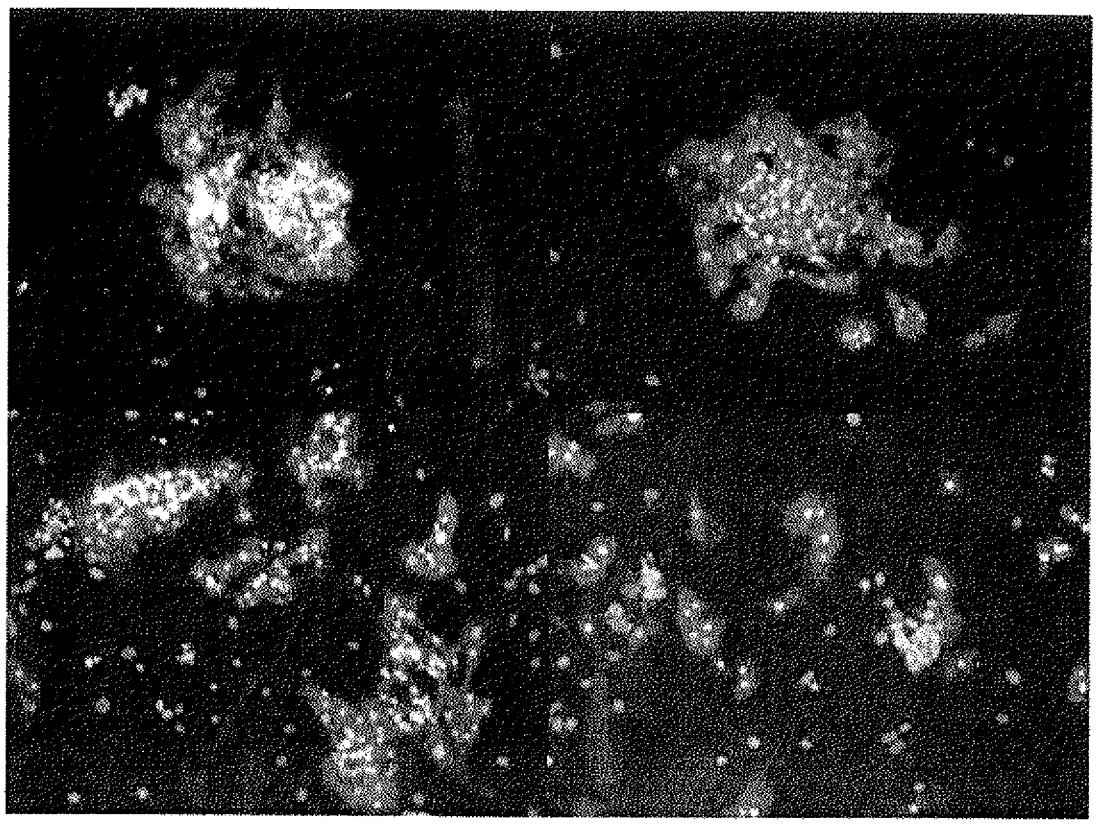
FIG. 9 shows cardiomyocyte-specific staining images for cells which are selected and collected by culturing the cells under a sugar-free/serum-free and a lactic acid-supplemented condition.

As a result, it was demonstrated that the proportion of the cardiomyocytes within, the masses purified by this Example accounted for 80% of the total number of the cells (FIG. 9).

Example 8

Purification of the Cardiomyocytes by Culturing Under a Serum-Free/a Mildly-Acidic/a Low Calcium/a Sugar-Free and a Lactic Acid-Supplemented Condition This Example aims at studying the complexed effect of serum depletion, a mildly-acidic pH condition, a low calcium condition, and sugar depletion on the cell masses (the embryoid bodies) containing the cardiomyocytes, more specifically the complexed effect of serum depletion, a mildly-acidic pH condition, a low calcium condition, and sugar depletion on selection of the cardiomyocytes from the cell masses (the embryoid bodies), by culturing the cell masses (the embryoid bodies) in the culture medium under a serum-free, a mildly-acidic, a calcium-free, and a sugar-free condition.

In this Example, 75 mouse ES cells per one EB were cultured as the cell masses for 5 days from the start of the differentiation in the culture medium [α-MEM (SIGMA), 10% FBS (EQUITEC BIO), penicillin/streptomycin (GIBCO)] using the hanging drop method to form embryoid bodies, which were then differentiated into the cell masses (the embryoid bodies) containing the programmed cardiomyocytes. In this Example, after 5 days from the start of the differentiation culture of the cells, the stage when any autonomously pulsating cardiomyocytes have not yet observed, the cells were further cultured in the serum-free MEM culture medium (GIBCO) supplemented with insulin/transferrin/selenium (GIBCO) for additional 2 days (the same results are produced in both situations when the culture was started on 4 days or 6 days from the start of the differentiation culture). The thus obtained masses of the programmed cardiomyocytes were cultured for additional 2 days to differentiate into the cardiomyocytes. At this stage, the cell masses containing the cardiomyocytes at high rate were generated.

Figure 10:
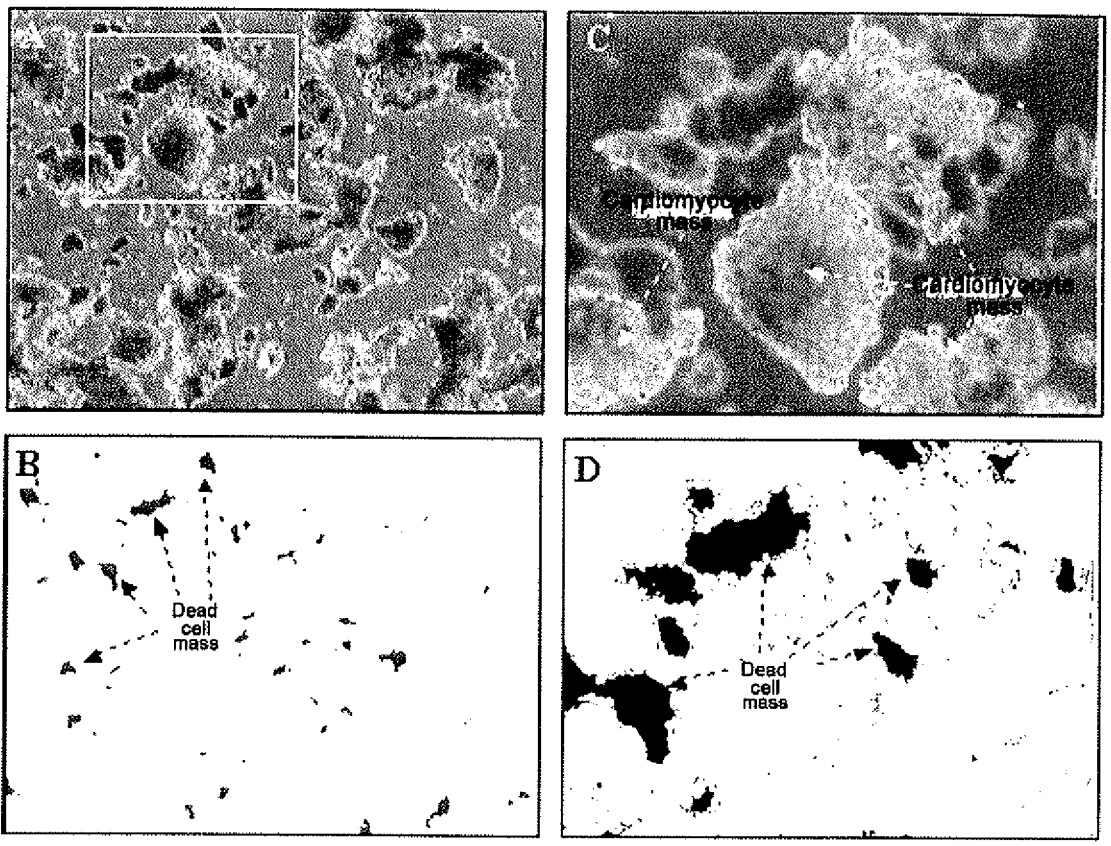
FIG. 10 shows masses of cardiomyocytes and masses of dead cells which are just selected by culturing the cells under a serum-free/mildly-acidic/low calcium/sugar-free and a lactic acid-supplemented condition.

Then, the cell masses were washed 4-5 times using D-MEM culture medium (sugar-free) (GIBCO) to thoroughly eliminate sugars from the culture medium, and then were cultured for 7 days in D-MEM culture medium (GIBCO) supplemented with a lactic acid at a final concentration of 1 mM (it is necessary to visually measure the viability of the autonomously pulsating cardiomyocytes and other cells in the multiple times of experiments and to adjust the culture period between 5-10 days on the basis of the viability). As shown in FIG. 10, the masses of the cardiomyocytes consisting only of the viable cardiomyocyte were formed.

The cell masses were treated with 0.01-0.1% of collagenase which selectively digests the collagen, one of the extracellular matrix proteins, at 37° C. for 20 minutes. After treatment with collagenase, the cell masses were washed using the buffer having a physiological osmotic pressure (116 mM NaCl, 20 mM Hepes, 12.5 mM $NaH_2PO_4$, 5.6 mM glucose, 5.4 mM KCl, 0.8 mM $MgSO_4$, pH 7.35). The cell masses were washed 4-5 times by solution exchange through the commercially available membrane having pores of 40 μm in diameter. As a result, the cell masses consisting only of the cardiomyocytes and high-density aggregates consisting of the dead cells were collected (FIG. 10A). FIG. 10C shows a magnified image of the framed rectangle region in FIG. 10A. Further, the location of the dead cells in FIGS. 10A and 10C are shown in FIGS. 10B and 10D, respectively.

Figure 11:
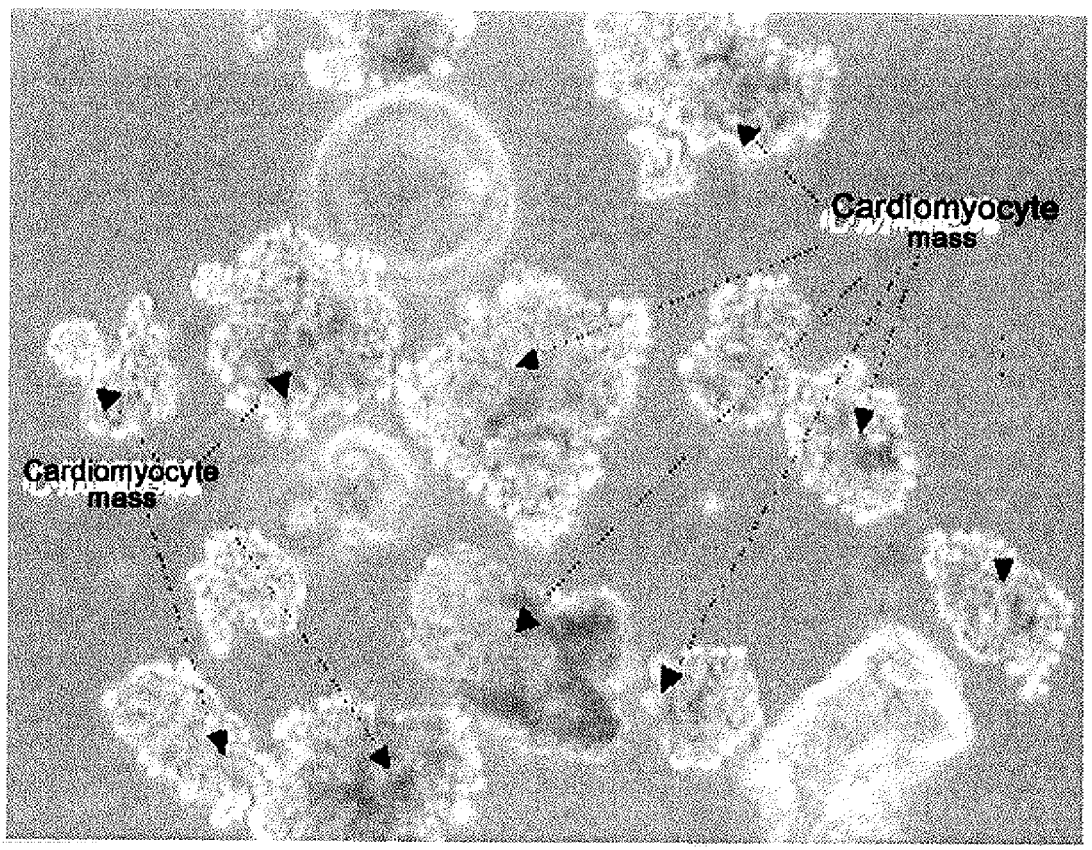
FIG. 11 shows a result of a method for eliminating high density aggregates consisting of the masses of the dead cells using density-gradient centrifugation.
Figure 12:
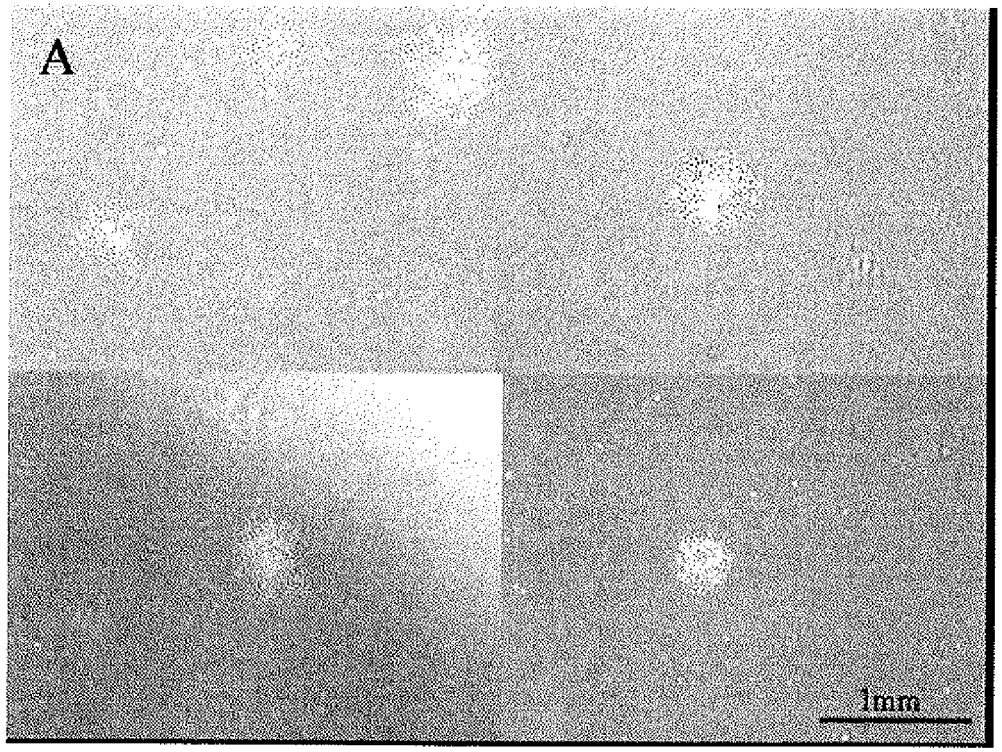
Figure 1:
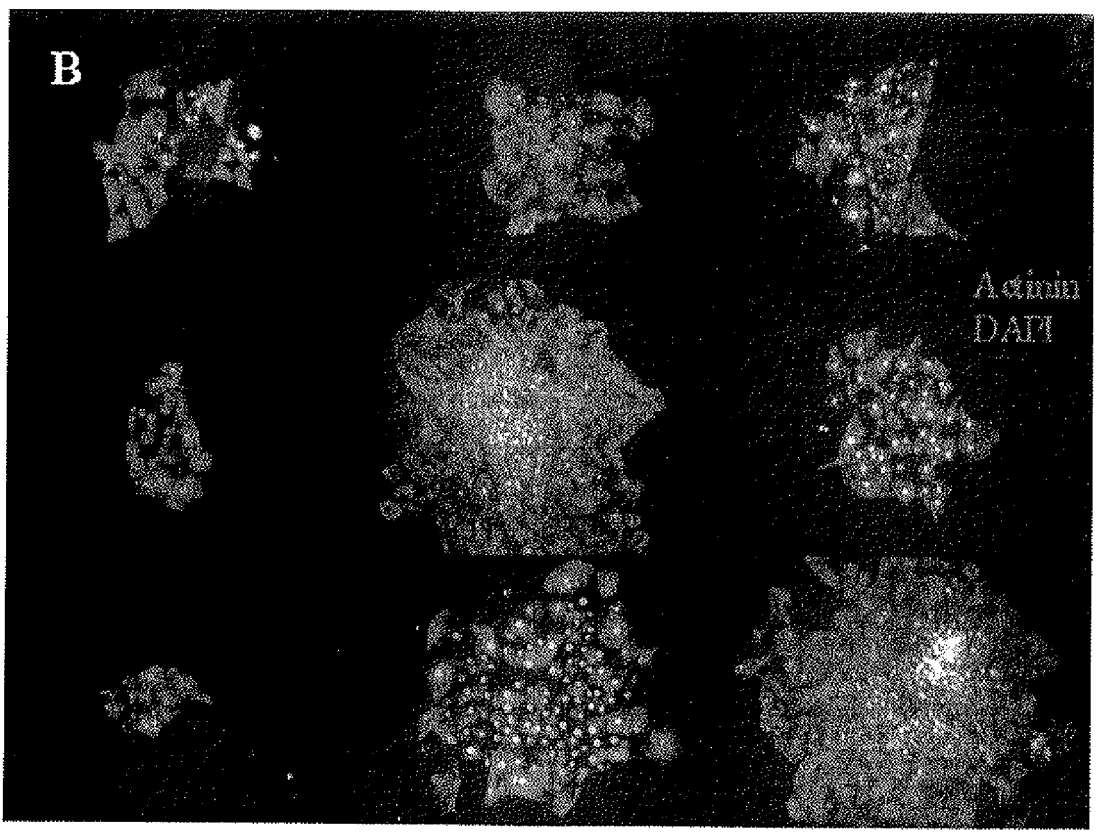
Figures 2, 12:
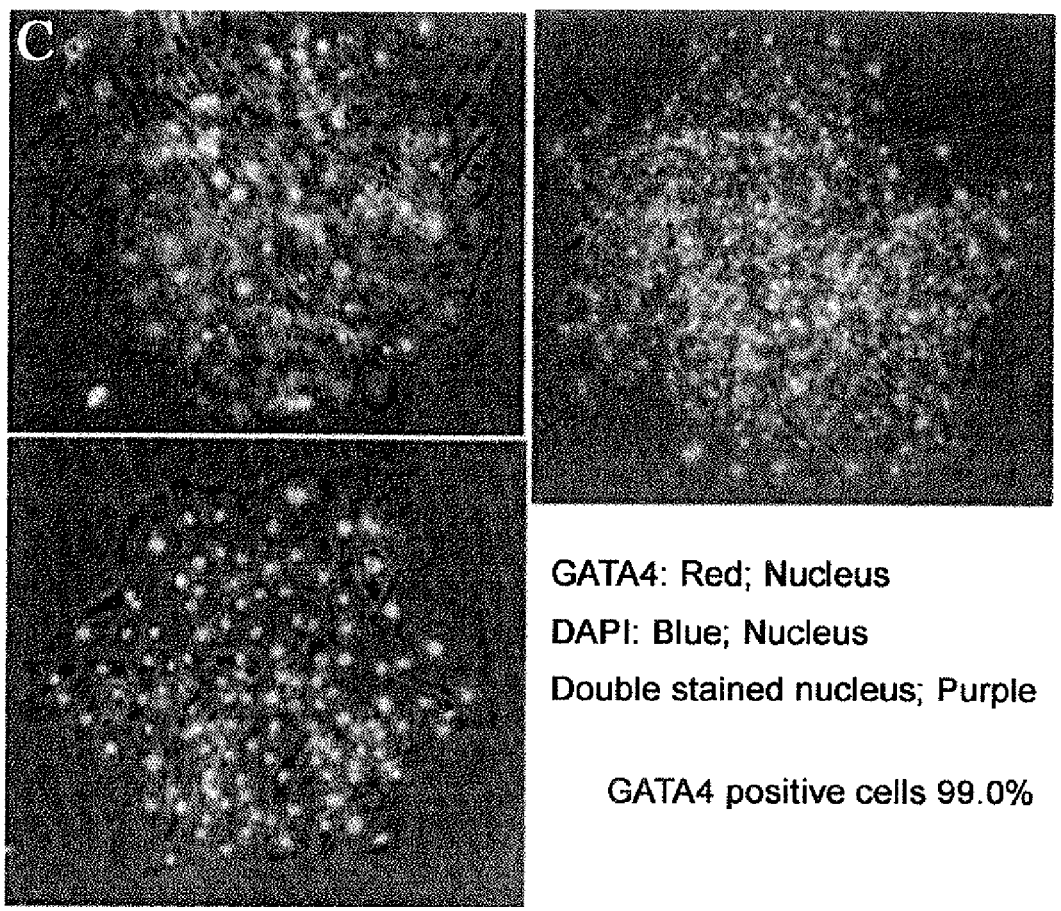

It was demonstrated in this Example that the high-density aggregates consisting of the dead cells shown in FIG. 10 could be selectively removed using an appropriate density-gradient centrifugation, more specifically using the density-gradient centrifugation with 58.5% Percoll™ (Pharmacia) (FIG. 11). Then, the thus obtained cell masses were cultured and immunostained using the anti-sarcomere -Actinin antibody and an anti-GATA4 antibody (Santacruz) as an indicator of the cardiomyocytes. FIG. 12A shows adhered masses of the cardiomyocytes. There were some suspended dead cells around the periphery of the adhered masses, while no adhered non-cardiomyocyte was observed. FIG. 12B shows fluorescent images developed by immunostaining the cell masses of FIG. 12A with sarcomere-Actinin (Red; cytoplasm) and DAPI (Molecular probe) (Blue; nuclei), FIG. 12C shows fluorescent images developed by immunostaining the cell masses of FIG. 12A with GATA4 (Red; nuclei) and DAPI (Blue; nuclei). Co-stained nuclei are purple colored, As a result, it was demonstrated that the proportion of the cardiomyocytes within the masses purified by this Example accounted for 99.0% of the total number of the cells (FIG. 12C).

Example 9

Purification of the Cardiomyocytes by Culturing Under a Serum-Free/a Mildly-Acidic/a Low Calcium/a Sugar-Free and an Aspartic Acid/a Glutamic Acid-Supplemented Condition This Example aims at studying the effect of compensation of an aspartic acid/a glutamic acid on the cell masses (the embryoid bodies) containing the cardiomyocytes, more specifically the effect of compensation of an aspartic acid/a glutamic acid on selection of the cardiomyocytes from the cell masses the embryoid bodies), by culturing the cell masses (the embryoid bodies) in culture medium supplemented with an aspartic acid/a glutamic acid under serum-free, a mildly -acidic, calcium-free, and a sugar-free condition.

In this Example, 75 mouse ES cells per one EB were cultured as the cell masses for 5 days from the start of the differentiation in the culture medium [α-MEM (SIGMA) 10% EDS (EQUITEC BIO) penicillin/streptomycin (GIBCO)] using the hanging drop method to form embryoid bodies, which were then differentiated into the cell masses the embryoid bodies) containing the programmed cardiomyocytes. In this Example, after 5 days from the start of the differentiation culture of the cells, the stage when any autonomously pulsating cardiomyocytes have not yet observed, the cells were cultured in the culture medium under a serum-free, a mildly-acidic pH, and a low calcium condition for 3 days (the same results are produced in both situations when the culture was started on 4 days or 6 days from the start of the differentiation culture). At this stage, the cell masses generated contained the cardiomyocytes at extremely high rate. Then, the cell masses were washed 4-5 times using D-MEM culture medium (sugar-free) (GIBCO) to thoroughly eliminate sugars in the culture medium by solution exchange through the commercially available membrane having pores of 40 μm in diameter. Finally, the cell masses were cultured for 5 days in DMEM culture medium (sugar-free) supplemented with 20 mg/L of a glutamic acid (SIGMA) and 20 mg/L of an aspartic acid (SIGMA) (it is necessary to visually measure the viability of the autonomously pulsating cardiomyocytes and other cells in the multiple times of experiments and to adjust the culture period between 3-10 days on the basis of the viability). As a result, the formed masses of the cardiomyocytes consisted only of the cardiomyocytes. The cell masses were treated, while shaking, at 37° C. in the water bath for 20 minutes, with 0.03% of collagenase which selectively digests the collagen, one of the extracellular matrix proteins. After treatment with collagenase, the cell masses were washed with an isotonic solution having a physiological osmotic pressure (116 mM NaCl, 20 mM Hepes, 12.5 mM $NaH_2PO_4$, 5.6 mM glucose, 5.4 mM KCl, 0.8 mM $MgSO_4$, pH 7.35), The cell masses were washed 4-5 times by solution exchange through the commercially available membrane having pores of 40 μm in diameter. As a result, the collected cell masses consisted only of the cardiomyocytes. The thus obtained cell masses were cultured and immunostained using the anti-sarcomere-Actinin antibody and the anti-GATA4 antibody as indicators of the cardiomyocytes (FIG. 13).

Figure 13:
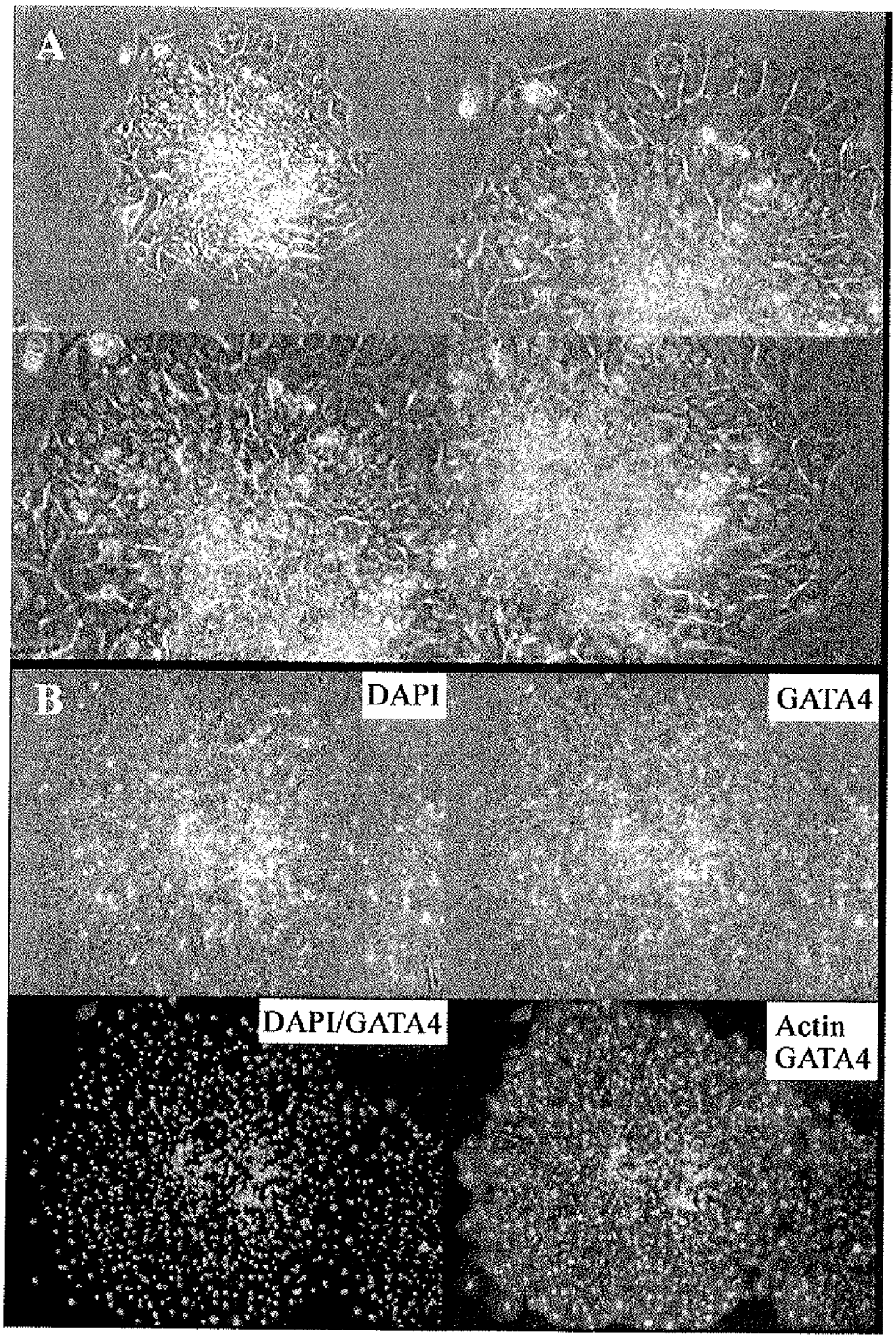
FIG. 13 shows the cardiomyocytes purified by culturing the cells under a serum-free/mildly-acidic/low calcium/sugar-tree and an aspartic acid/glutamic acid-supplemented condition.

Further, the cells were subjected to statistical analysis, in which the present data were compared with the known data (FIG. 13). FIG. 13A shows microscopic images of colonies of the autonomously pulsating cardiomyocytes, and FIG. 13B shows images of sarcomere-Actinin staining (Red; cytoplasm), GATA4 staining (Green; nuclei), and DAPI staining Blue; nuclei) for the colonies of the autonomously pulsating cardiomyocytes.

As a result, it was shown that the proportion of the cardiomyocytes within the masses purified by this Example accounted for 99.8% of the total number of the cells. It is demonstrated that this degree of purification was higher than the degrees shown by any known methods for purifying the cardiomyocytes (for example, FASEB J. 2000; 14: 2540-2548; J Clin Invest. 1996; 98: 216-224; FASEB J. 2003; 17: 740-742; J Mol Cell Cardiol. 2003; 35: 1461-1472). Therefore, the method of this Example enables purification of the cardiomyocytes at a high degree of purification and at a high yield (Table 1).

[Table 1]
Table 1: Comparison of purity and yield between the method of the present invention and the αMHC-promoter/neo method.

TABLE 1

Comparison of purity and yield between the method of the present invention and the αMHC-promoter/neo method.

| Preparation | Sarcomeric myosin positive cells | Sarcomeric myosin negative cells | Percent cardiomyocytes |
|---|---|---|---|
| No selection* | 11 | 2000 | 0.55 |
| Physical isolation‡ | 68 | 2000 | 3.4 |
| G418 selection§ | 791 | 3 | 99.6 |

| | Sarcomeric Actin GATA4 Positive cells | Sarcomeric Actin GATA4 Negative cells | |
|---|---|---|---|
| Hattori | 5041 | 10 | 99.8 |

| | Input ES cells | Output Cardiomyocytes |
|---|---|---|
| Field et al. | $10^6$ | $\approx 10^6$ |
| Hattori | 7500 | $\approx 15000$ |

Field et al. (J. Clin. Invest. 1996, Vol. 98, 216-224)

Example 10

Purification of the Cardiomyocytes Produced From Adult Stem Cells Derived From the Mouse Bone Marrow This Example aims at producing the cardiomyocytes from adult stem cells derived from the mouse bone marrow, called as the mesenchymal stem cells, which are then selected and purified.

The cardiomyocytes differentiated from the adult stem cells derived from the mouse bone marrow (female C3H/He mouse) were induced using the cells and the method described in WO01/048151. That is to say, CMG cells were cultured in the culture medium of IMDM (Iscove's Modified Dulbecco's Medium) (GIBCO) supplemented with 20% of fetal bovine serum (regarding the method for establishing CMG cells, see, J Clin Invest, March 1999, Vol. 103, p697-705), cultured for additional 24 hours in a culture medium supplemented with a final concentration of 3 μmol/l of 5-azacytidine (SIGMA), then cultured for 2-3 weeks in the culture medium above without 5-azacytidine, resulting in differentiation induction of the cardiomyocytes. After confirmation of the autonomously pulsating cardiomyocytes, the cells are cultured for 5 days in D-MEM culture medium (GIBCO) supplemented with 1 mM of a lactic acid under a serum-free/a mildly-acidic pH/a low calcium/a sugar-free condition. After the culture period, the dead cells were removed and the remaining viable cells were immunostained using the anti-sarcomere-Actinin antibody as an indicator of the cardiomyocytes.

Figure 14:
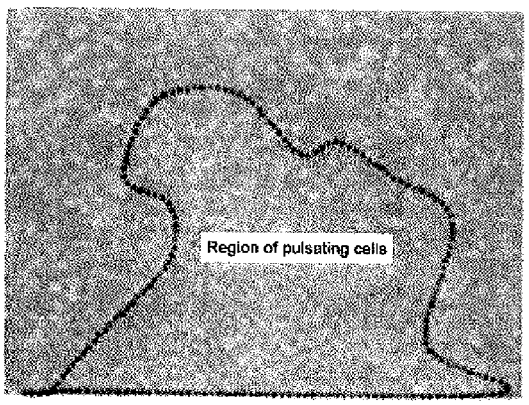
FIG. 14 shows results of purification of the cardiomyocytes from the bone marrow stem cells.
Figure 14:
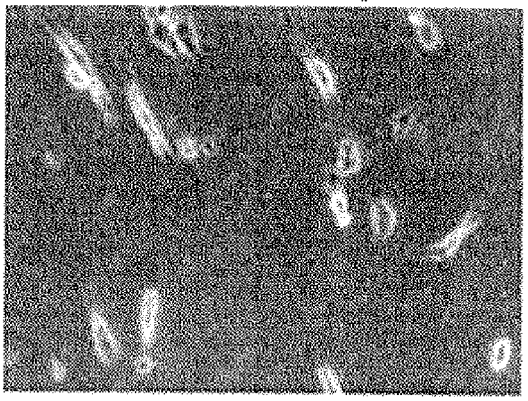
Figure 14:
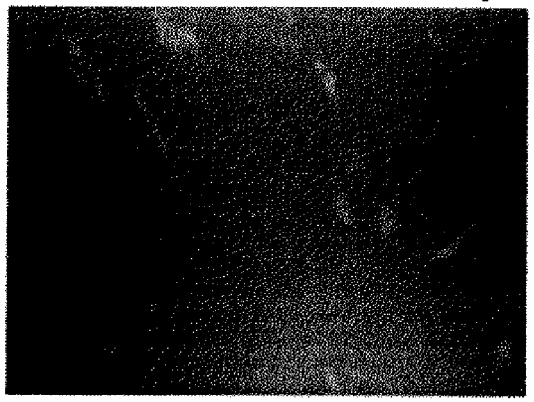

FIG. 14A shows appearance of the cultured cells before selection. In FIG. 14A, the region containing pulsating cells are shown by dotted line. FIGS. 14B-C show the cells selected. FIG. 14B shows a phase-contrast microscopic image, and FIG. 14C shows a fluorescent image immunostained for sarcomere-Actinin for the same field of view as FIG. 14B, respectively. As a result, it was demonstrated that the proportion of the cardiomyocytes within the masses produced by this Example accounted for about 90% of the total number of the cells (FIG. 14).

Example 11

Purification of the Cardiomyocytes Derived from the Mouse Fetuses

This Example aims at purifying the cardiomyocytes from the mouse fetuses.

First, mouse embryo at the 7th-9th day of embryonic life was removed from the maternal uterus, from which the extraembryonic tissue was carefully cleaned off, then pipetteing to disperse fetuses to separate cell masses. The thus obtained cell masses were cultured for 5 days in the culture medium supplemented with 0.5 mM of a lactic acid under serum-free/a mildly-acidic pH/a low calcium/sugar-free condition (it is necessary to visually measure the viability of the autonomously pulsating cardiomyocytes and other cells in the multiple times of experiments and to adjust the culture period between 3-10 days on the basis of the viability). The culture medium used was prepared by mixing Hank's BSS [sugar-free]:RPMI [sugar-free]=9:1. The purified cardiomyocytes were subjected to adhesion. culture, and after the culture, the dead cells were removed and the remaining viable cells were immunostained for sarcomere-Actinin (Green; cytoplasm) as an indicator of the cardiomyocytes, and DAPI (Red; nuclei).

Figure 15:
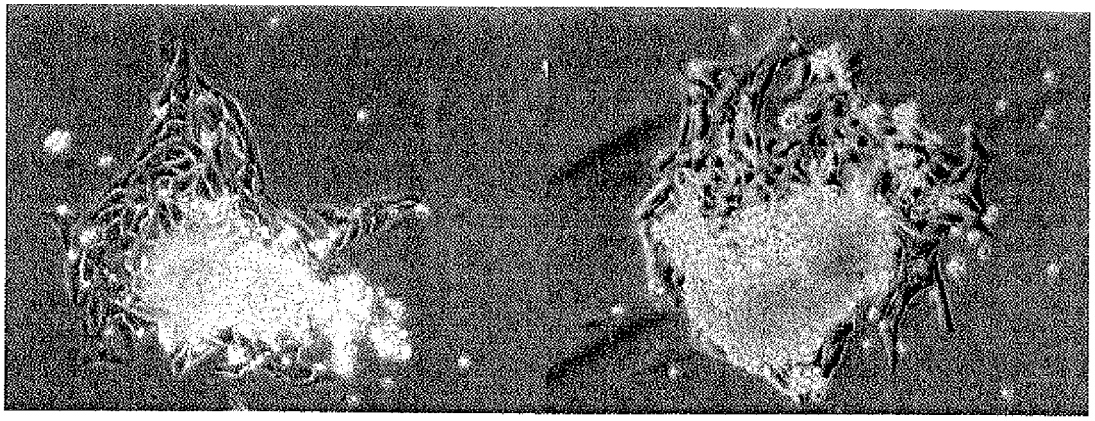
FIG. 15 shows results of purification of the cardiomyocytes from the fetuses.
Figure 15:
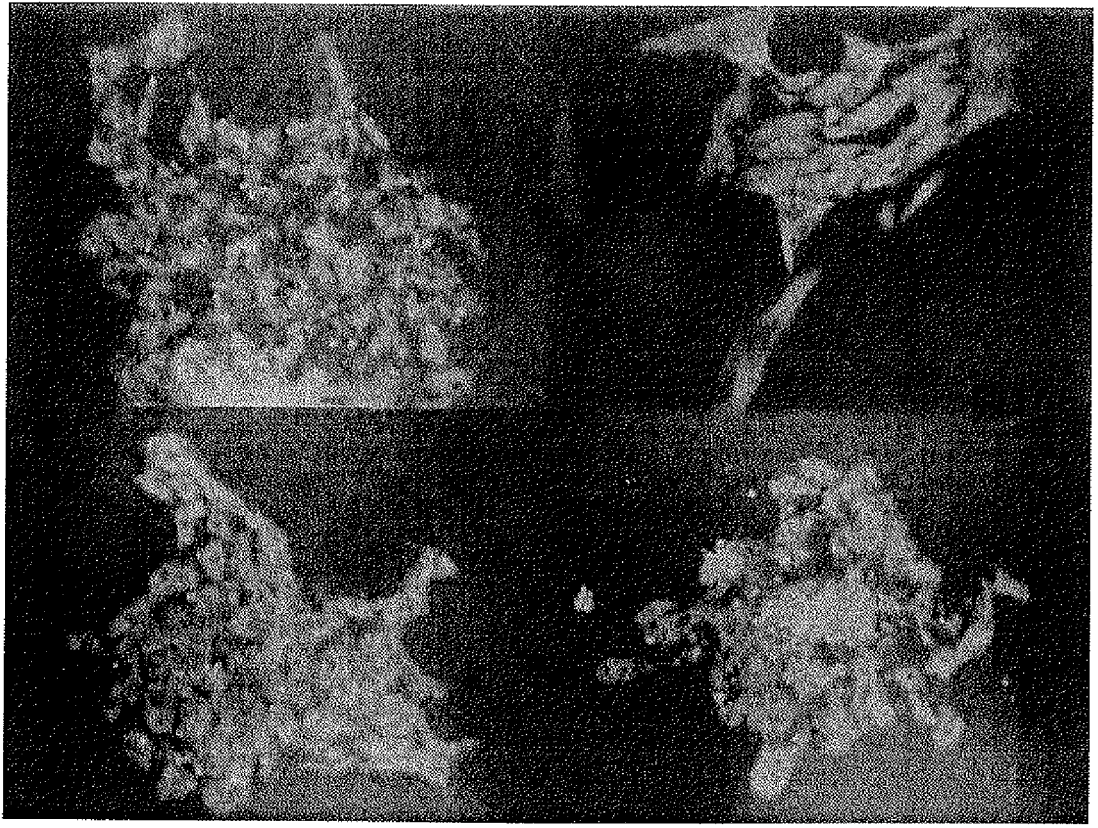

FIG. 15A shows phase-contrast microscopic images of two colonies showing the pulsating cell population. FIG. 15B shows merged images of sarcomere-Actinin staining and DAPI staining for four colonies. As a result, it was demonstrated that the proportion of the cardiomyocytes within the masses produced by this Example accounted for about 99% of the total number of the cells (FIG. 15).

Example 12

Purification of the Cardiomyocytes Under a Serum-Free/a Mildly-Acidic/a Low Calcium/a Sugar-Free, and a Pyruvic Acid-Supplemented Condition This Example aims at studying the effect of compensation of a pyruvic acid on the cell masses (the embryoid bodies) containing the cardiomyocytes, more specifically the effect of compensation of a pyruvic acid on selection of the cardiomyocytes from the cell masses (the embryoid bodies), by culturing the cell masses (the embryoid bodies) in the culture medium supplemented with a pyruvic acid under serum-free, a mildly-acidic pH, calcium-free, and sugar-free condition.

In this Example, 75 mouse ES cells per one EB were cultured as the cell masses for 5 days from the start of the differentiation in the culture medium [α-MEM (SIGMA) 10% FBS (EQUITEC BIO) penicillin/streptomycin (GIBCO)] using the hanging drop method to form embryoid bodies, which were then differentiated into the cell masses (the embryoid bodies) containing the programmed cardiomyocytes. In this Example, after 5 days from the start of the differentiation culture of the cells, the stage when any autonomously pulsating cardiomyocytes have not yet observed, the cells were cultured for additional 2 days in the culture medium in the serum-free MEM culture medium (GIBCO) supplemented with insulin/transferrin/selenium (GIBCO) (the same results are produced in both situations when the culture was started on 4 days or 6 days from the start of the differentiation culture). The thus obtained masses of the programmed cardiomyocytes were cultured for additional 2 days to differentiate into the cardiomyocytes. At this stage, the cell masses generated contained the cardiomyocytes at extremely high rate. Then, the cell masses were washed 4-5 times using D-MEM culture medium (sugar-free) (GIBCO) to thoroughly eliminate sugars in the culture medium by solution exchange through the commercially available membrane having pores of 40 μm in diameter. After the washing step, the cell masses were cultured for 5 days in D-MEM culture medium (sugar-free) (GIBCO) supplemented with a final concentration of 1 mM of a pyruvic acid.

Figure 16:
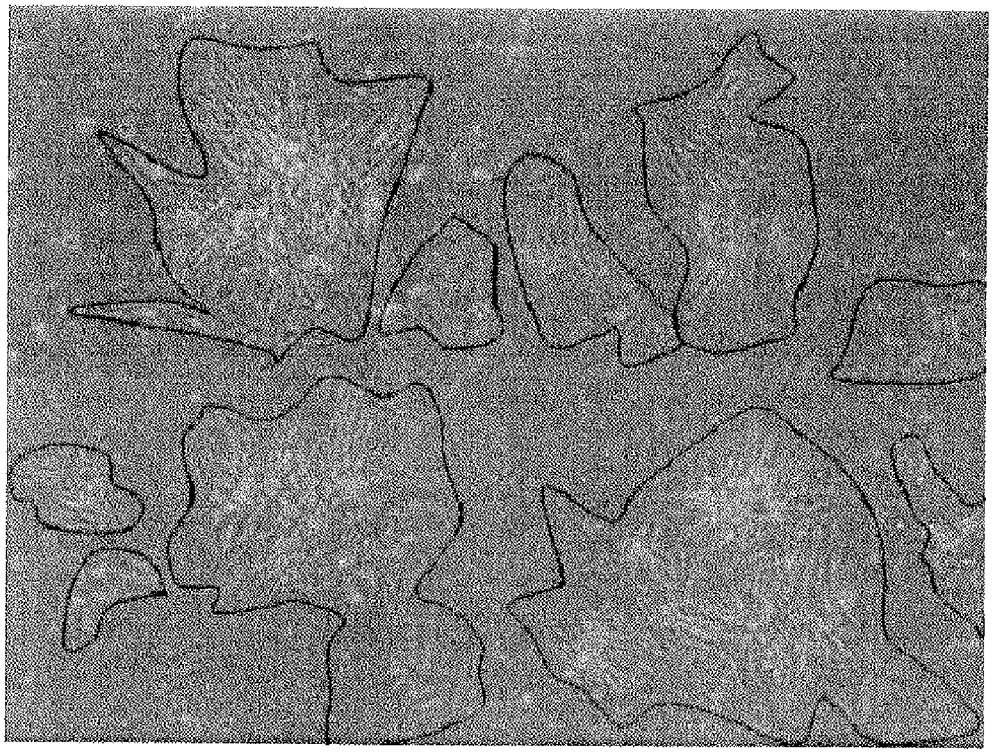
FIG. 16 shows regions containing autonomously pulsating cells under a serum-free/mildly-acidic/low calcium/sugar-free and a pyruvic acid-supplemented condition.

The cell masses were then treated, while shaking, with 0.05% of collagenase Type 3 (Worthington Biochemical Corp) which selectively digests the collagen, one of the extracellular matrix proteins, at 37° C. for 20 minutes. After treatment with collagenase, the cell masses were washed with an isotonic solution having a physiological osmotic pressure (116 mM NaCl, 20 mM Hepes, 12.5 mM $NaH_2PO_4$, 5.6 mM glucose, 5.4 mM KCl, 0.8 mM $MgSO_4$, pH 7.35). As a result, it was demonstrated that the proportion of the autonomously pulsating cells within the masses purified by this Example accounted for more than 90% of the total number of the cells (FIG. 16).

Example 13

Selection and Purification of the Cardiomyocytes Derived From the Primate Marmoset Embryonic Stem Cells Under a Sugar-Free/a Serum-Free, and a Lactic Acid -Supplemented Condition This Example aims at studying the complexed effect of serum depletion and sugar depletion on the cell masses (the embryoid bodies) containing the cardiomyocytes, more specifically the complexed effect of serum depletion and sugar depletion on selection of the cardiomyocytes from the cell masses (the embryoid bodies) derived from the primate marmoset embryonic stem cells, by culturing the cell masses (the embryoid bodies) in the serum-free and sugar-free culture medium.

The marmoset embryonic stem cells are available from Central institute for Experimental Animals (Kawasaki, Japan). The marmoset embryonic stem cells were cultured while maintaining undifferentiated state using the growth inactivated mouse embryonic fibroblasts (MEF) which were treated with mitomycin C treatment. The culture medium [KO-DMEM (GIBCO), 20% KO-SERUM (GIBCO), 1.6 mM L-glutamine, 0.1 mM non-essential amino acid (MEM), 0.2 mM β-mercaptoethanol (2-ME; SIGMA), 100 IU/ml penicillin, 100 82 g/ml streptomycin sulfate, and 8 ng/ml of a recombinant human leukemia inhibitory factor (LIF; Chemicon), a recombinant human basic fibroblast growth factor (bFGF; Peprotech)] was used, Upon passaging, 0.1% type III collagenase (Wortington) was used at 37° C. for 10 minutes to separate ES colonies.

Subsequently, to separate MEF and ES with each other, the solution was passed through mesh baring pores of 100 μm in diameter, thereby obtained cell masses which cannot be pass through the mesh baring pores of 40 μm in diameter. These cell masses are exactly the purified masses of ES cells. Upon differentiation, the cell masses containing 50-1000 of ES cells per one EB were cultured as an embryoid body for total 15-30 days using a bacterial dish method, then to differentiate into the embryoid bodies containing the cardiomyocytes. The culture medium used for the differentiation was the same as the culture medium described in the present Example, except for bFGF [i.e., KO-DMEM (GIBCO), 20% KO-SERUM (GIBCO), 1.6 mM L-glutamine, 0.1 mM non-essential amino acid (MEM), 0.2 mM β-mercaptoethanol (2-ME; SIGMA), 100 IU/ml penicillin, 100 μg/ml streptomycin sulfate, and 8 ng/ml of a recombinant human leukemia inhibitory factor (LIF; Chemicon)].

To eliminate the sugars as much as possible from the culture medium, the embryoid bodies were transferred to a centrifuging tube, were washed five times with D-MEM culture medium (sugar-free) (GIBCO), and were finally cultured for 15 days in D-MEM culture medium (sugar-free) (GIBCO) supplemented with 1 mM of a lactic acid. Since the in vivo concentration of a lactic acid increases to about 4 mM under the physiological condition, the concentration of a lactic acid of "1 mM" used in the method of this Example falls within the physiological range.

Figure 17:
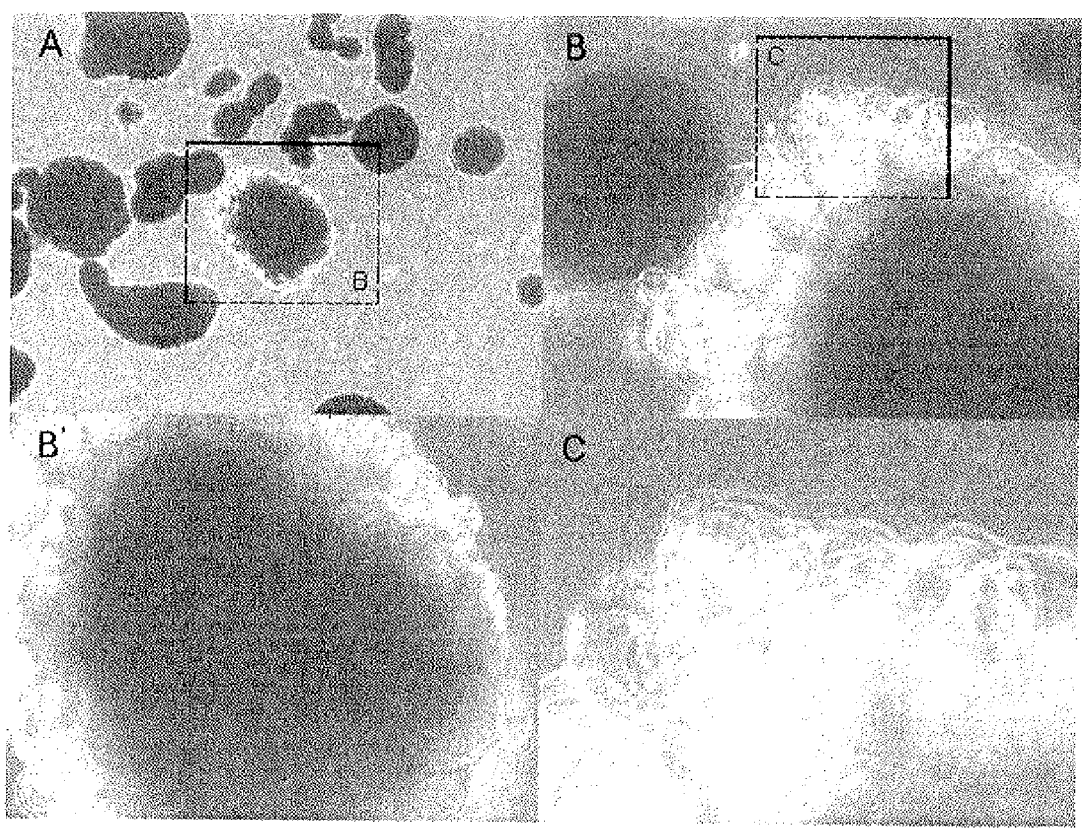
FIG. 17 shows masses of marmoset cardiomyocytes which are selected by culturing the cells for 15 days under a sugar-free/serum-free and a lactic acid-supplemented condition.

The appearance of cell masses after culturing for 15 days are shown in FIG 17. As shown in FIG. 17, it was shown from this result that formed bubble-like structure of the cells consisted of the cardiomyocytes as viable cells. That is to say, FIGS. 17A-C show that the cardiomyocytes forming the bubble-like structure were selectively viable in the culture medium under a sugar-free a lactic acid-supplemented (1 mM) condition. FIGS. 17A show that a part of or whole embryoid bodies with greatly reduced optical transparency have already undergone cell death. Also, in the cases of the embryoid bodies shown in FIG. 17B and FIG. 17B', the cells having the bubble-like structure on the embryoid body surface were viable. FIG. 17C is a magnified view of FIG. 17B.

Figure 18:
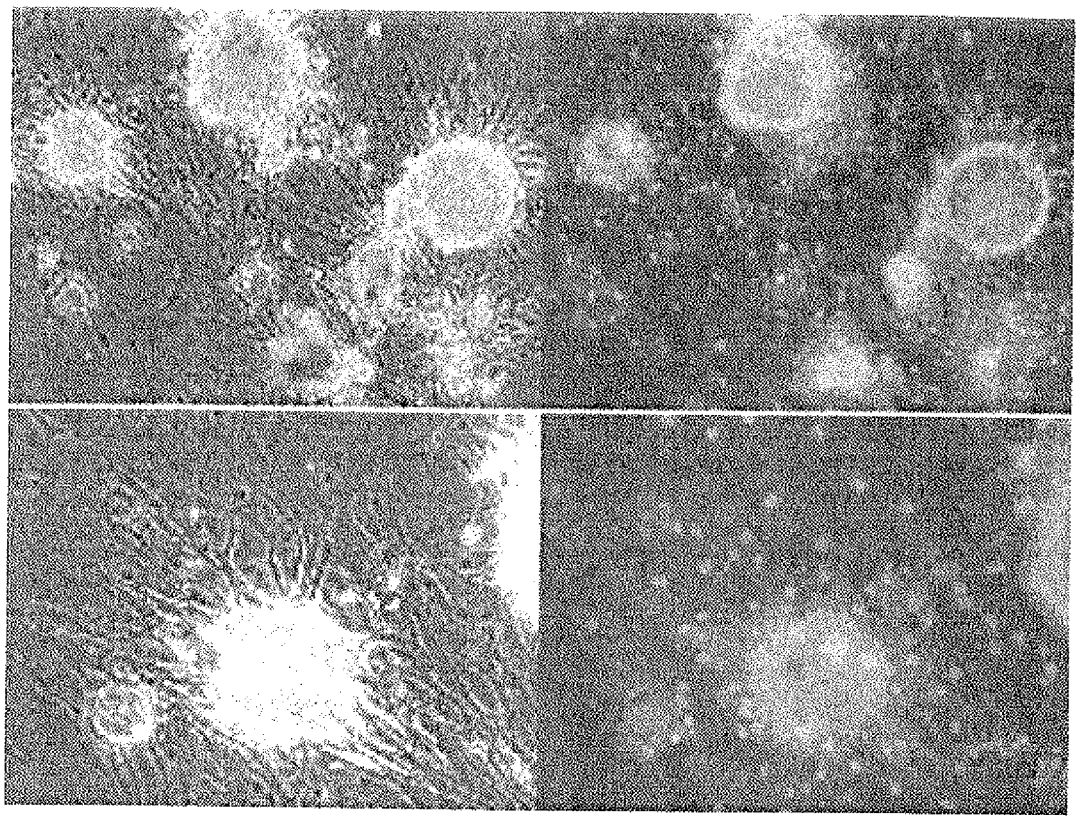
FIG. 18 shows cardiomyocyte-specific staining images for marmoset cells which are selected and collected by culturing the cells under a sugar-free/serum-free and a lactic acid-supplemented condition.

The thus obtained embryoid bodies were cultured for 3-7 days in the same volume of the same culture medium (bFGF-free). The viable cardiomyocytes resume autonomous pulsating. After reaching the stabilized state, the dead cells were separated from the cardiomyocytes by shaking the embryoid bodies in the presence of 0.1% type III collagenase (Wortington) for 10 minutes at 37° C. The dead cells were eliminated by the method disclosed in Example 8. The thus obtained embryoid bodies were adhered on a fibronectin (SIGMA)-coated cell culture dish (FIG. 18, left). After fixation with 4% paraformaldehyde, the embryoid bodies were stained with the anti-Actinin antibody (SIGMA) as in Example 8and were stained with the anti-Nkx2.5 antibody (Santacruz) as in Example 4 (FIG. 18, right, respectively).

As a result, it was demonstrated that the cardiomyocytes were selectively obtained by culturing marmoset embryonic stem cells under a sugar-free/a serum-free and a lactic acid-supplemented condition.

Example 14

Transplantation of the Cardiomyocytes Derived From Primate Marmoset Embryonic Stem Cells Into the Heart of an Immunodeficient on and Confirmation of Engraftment Thereof This Example aims at studying transplantation of the cardiomyocytes derived from the primate marmoset embryonic stem cells into the heart and engraftment within the body.

The purified marmoset cardiomyocytes prepared by the method of Example 13 were suspended in a buffering solution having physiological osmotic pressure (116 mM NaCl, 20 mM Hepes, 12.5 mM $NaH_2PO_4$, 5.6 mM glucose, 5.4 mM KCl, 0.8 mM $MgSO_4$, pH 7.35) supplemented with 0.2% type III collagenase (Wortington) and 0.125% Trypsin (GIBCO). The suspended solution were treated, while shaking, for 20 minutes at 37° C. in a syringe attached to a 29 gauge needle (Terumo). About 1-30 small cell masses consisting of the cardiomyocytes were prepared to use for transplantation. The above buffer having physiological salt concentration containing the cardiomyocytes 100 μL was aspirated.

A 7-week old male NOD-SCID mouse, immunodeficient mouse (Clea Japan, Inc.) was anaesthetized by inhalation anesthetic FORANE (isoflurane) (Abbott Japan). Then, the thorax of the mouse was opened under the respiration control under artificial respiration using intratracheal intubation. An injection needle was inserted into the wall of the exteriorized heart in the direction from the cardiac apex to the cardiac base, and then about 30 μL of suspended solution per site was injected in the wall of the heart tissue. Then the thorax of the mouse was closed, anesthesia was ended and the mouse was continued maintaining.

Figure 19:
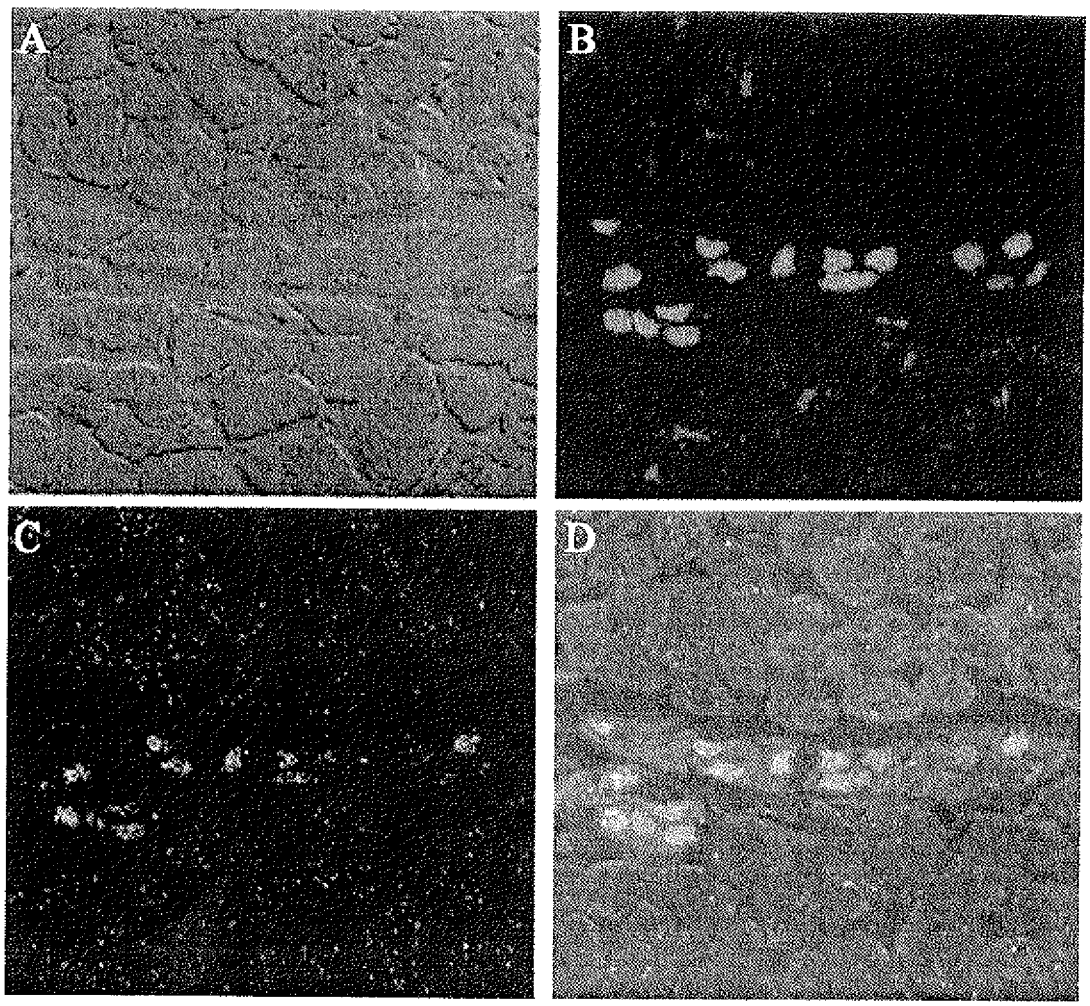
FIG. 19 shows that marmoset cells which are selected and collected by culturing under a sugar-free/serum -free and a lactic acid-supplemented condition are successfully engrafted inside the heart of a recipient.

After 15 days from the transplantation, the heart of the mouse was excised under anesthesia, which was fixed in 4% paraformaldehyde. Frozen sections of 10 μm in thick were prepared and immunostained using a goat anti-Nkx2.5 antibody (Santacruz) as a primary antibody and a donkey anti-goat antibody-Alexa 488 (developed in green) (Molecular probes) as a second antibody (FIG. 19B), or immunostained using a mouse anti-sarcomere-Actinin antibody (SIGMA) as a primary antibody and a rabbit anti-mouse antibody-Alexa 594 (developed in red) (Molecular probes) as a second antibody (FIG. 19D).

On the other hand, a mouse anti-human nuclear antigen antibody (which reacts with any nuclear antigen across the every primate species) (Chemicon) and a goat anti-mouse antibody-Alexa 633 (Molecular probes) are reacted together in vitro to form a complex. Next, a normal mouse serum was used to inhibit the reactivity of the excess of a goat anti-mouse antibody-Alexa 633 (infrared). The thus prepared antibody complex was reacted with the above frozen sections to develop three colors (FIGS. 19B-19D).

All immunostaining images were taken using a confocal microscope (Carl Zeiss). The results were shown in FIG. 19.

As a result, it was demonstrated that the cells having a larger nucleus shown in the figure were derived from marmoset. That is to say, it was demonstrated in this figure that some primate cells expressing Nkx2.5, an indicator marker specific for the cardiomyocytes, were seen in the cardiomyocytes stained with Actinin. This means that the cardiomyocytes derived from marmoset ES cells were successfully engrafted in the mouse heart.

Example 15

Selection and Preparation of the Cardiomyocytes Derived From Human Embryonic Stem Cells Under a Sugar-Free/a Serum-Free and a Lactic Acid-Supplemented Condition This Example aimed at studying the complexed effect of serum depletion and sugar depletion on the cell masses (the embryoid bodies) containing the cardiomyocytes, more specifically the complexed effect of serum depletion and sugar depletion on selection of the cardiomyocytes from the cell masses (the embryoid bodies) derived from human embryonic stem cells, by culturing the cell masses (the embryoid bodies) in a serum-free and a sugar-free culture medium.

Human embryonic stem cells were obtained from the Stem Cell Research Center (the Institute for Frontier medical Sciences, Kyoto University) (the Center for the ES cells based on the National Bioresourse Project). The human embryonic stem cells were cultured while maintaining undifferentiated state using the growth inactivated mouse embryonic fibroblasts (MEF) which were treated with mitomycin C treatment. The culture was conducted using a culture medium [F12/DMEM (1:1) (SIGMA, product number D6421), 20% KO-SERUM (GIBCO), 1.6 mM L-glutamine, 0.1 mM non-essential amino acid (MEM), 0.1 mM β-mercaptoethanol (2-ME; SIGMA), 100 IU/ml penicillin, 100 μg/ml streptomycin sulfate, and a recombinant human basic fibroblast growth factor (bFGF; Peprotech)]. Upon passaging, 0.1% type III collagenase (Wortington) was used at 37° C. for 10 minutes to separate ES colonies, Subsequently, to separate MEF and ES with each other, the solution was passed through mesh having pores of 40 μm, thereby obtained cell masses which could not be pass through the mesh having pores of 40 μm. in diameter. These cell masses were purified masses of ES cell. Upon differentiation, cell masses containing 50-1000 of ES cells per one EB were cultured as an embryoid body for total 15-30 days using a bacterial dish method (using the culture medium described above except that in the absence of bFGF), then to differentiate into the embryoid bodies containing the cardiomyocytes. To eliminate the sugars as much as possible from the culture medium, embryoid bodies were transferred to a centrifuging tube, were washed five times with D-MEM culture medium (sugar-free) (GIBCO, product number 11966), and were finally cultured for 15 days in D-MEM culture medium (sugar-free) (GIBCO, product number 11966) supplemented with 1 mM of a lactic acid. Since the in vivo concentration of a lactic acid increases to about 4 mM under the physiological condition, the concentration of a lactic acid of "1 mM" used in the method of this Example falls within the physiological range.

Figure 20:
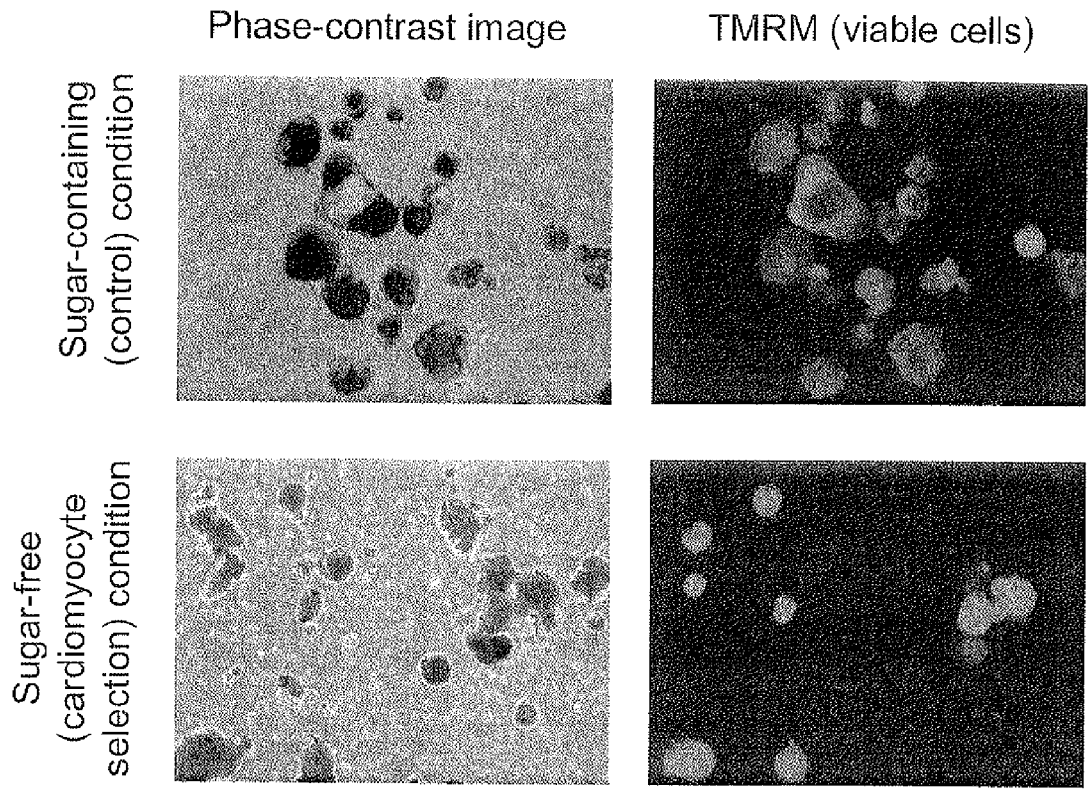
FIG. 20 shows images of the cell masses derived from human embryonic stem cells which were obtained by culturing under a sugar-containing (control) condition (i.e., control condition) and appearance of the cell masses derived from the human embryonic stem cells which were obtained by the cardiomyocyte selective culture under a sugar-free (cardiomyocyte selection) condition for 15 days (i.e., cardiomyocyte selection condition).

Appearances of the cell masses cultured under a sugar-containing condition (control condition) and the cell masses cultured for 15 days under a sugar-free condition for cardiomyocyte selection (cardiomyocyte selective condition) are shown in FIG. 20, left panel, as phase contrast images. To demonstrate whether these cells are viable or not, the cells were stained with TMRM (Molecular Probes), which can detect membrane potential (an indicator of viable cells) and generate fluorescence depending on the membrane potential (FIG. 20, right panel). As shown in FIG. 20, upper panel, all embryoid bodies of the sugar-containing (control) condition group generate fluorescence (i.e., all embryoid bodies are composed of viable cells); while, as shown in FIG. 20, lower panel, the cell masses which did not generate fluorescence (i.e., the cell masses consisting of the dead cells) appeared by culturing under the sugar-free (cardiomyocyte selection) condition. Further, every cell masses which were viable under the sugar-free (cardiomyocyte selection) condition showed autonomous pulsating.

The thus obtained embryoid bodies were cultured for 3-7 days in the same volume of the same culture medium (bFGF-free). The viable cardiomyocytes resume autonomous pulsating. After reaching the stabilized state, the dead cells were separated from the cardiomyocytes by shaking the embryoid bodies in the presence of 0.1% type III collagenase (Wortington) for 10 minutes at 37° C. The dead cells were eliminated. by the method disclosed in Example 8. Then, the embryoid bodies were adhered on a fibronectin (SIGMA)-coated cell culture dish.

Figure 21:
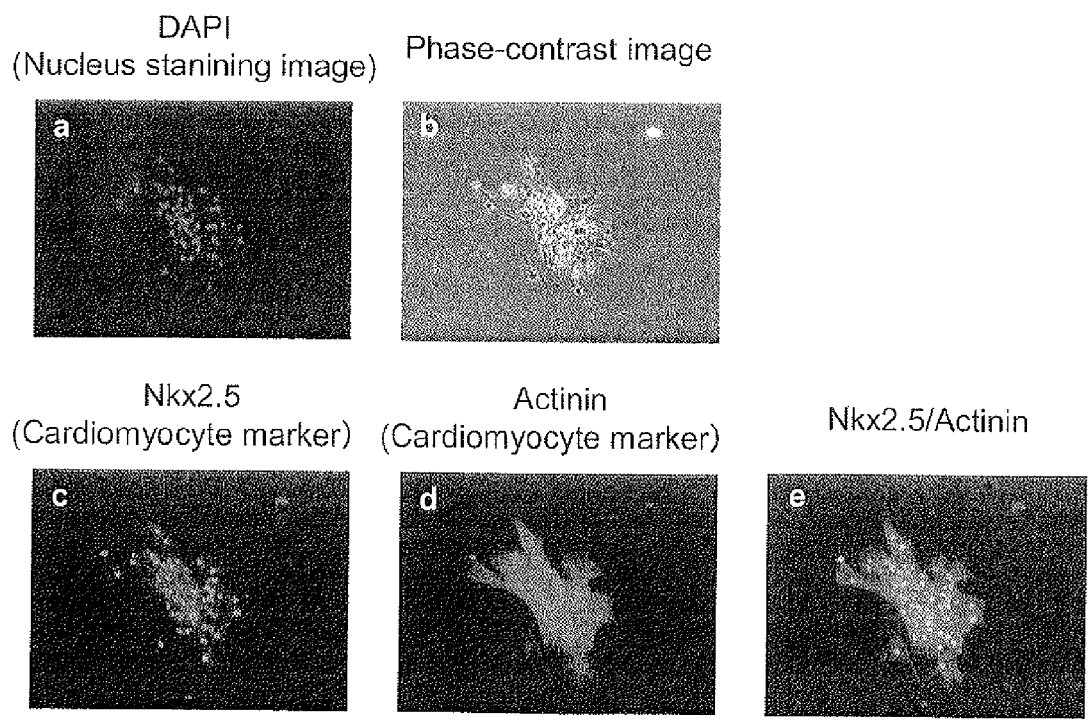
FIG. 21 shows immunostaining images of the cell masses derived from the human embryonic stem cells using an anti-Actinin antibody and an anti-Nkx2.5 antibody, wherein the cell masses were formed by the cardiomyocytes which resume autonomous pulsating. The cell masses were prepared by culturing the human embryonic stem cells under a sugar-free (cardiomyocyte selection) condition for 15 days and then changing the culture medium condition.

After fixation with 4% paraformaldehyde, the embryoid bodies were stained with the anti-Actinin antibody (SIGMA) as in Example 8 and were stained with the anti-Nkx2.5antibody (Santacruz) as in Example 4 (FIG. 21). As is shown. in this figure, the cellular nucleus stained by DAPI (FIG. 21*a*) were necessarily overlapped with the cellular nucleus immunostained, with the anti-Nkx2.5 antibody, an indicator marker specific for the cardiomyocytes (FIG. 21*c*). When an immunostained image with the anti-Actinin antibody, another indicator marker specific for the cardiomyocytes, (FIG. 21*d*) was merged with an immunostained image with the anti-Nkx2.5 antibody, it was found that the cells immunostained with the anti-Nkx2.5 antibody were completely overlapped with the cells immunostained with the anti-Actinin antibody (FIG. 21*e*).

It is clearly shown from this result that, when human embryonic stem cells are purified by culturing under a sugar-free/a serum-free and a lactic acid-Supplemented culture condition, the cardiomyocytes can selectively be collected.

The invention claimed is:

1. A method of selecting cardiomyocytes and/or Brachyury+/Nkx2.5-cells capable of differentiating into cardiomyocytes from a cell mixture containing cardiomyocytes, Brachyury+/Nkx2.5-cells, and non-cardiomyocyte cells comprising:
Culturing the cell mixture in a culture medium under the following conditions:
(i) a sugar-free condition or a condition wherein sugar content is 111.20 μM or less; and
(ii) one or more conditions selected from the group consisting of a low calcium condition, a low nutritional condition, a lactic acid-supplemented condition, an aspartic acid/glutamic acid-supplemented condition, and a pyruvic acid-supplemented condition to select the cardiomyocytes and/or Brachyury+/Nkx2.5-cells from the cell mixture, wherein the cell mixture is derived from totipotent cells, pluripotent cells, or stem cell having similar characteristics to those of embryonic stem cell through differentiation induction, wherein the low nutritional condition is a condition where the content of each nutritional component of the cultured medium is reduced to 10% or less of that of a culture medium selected from the group consisting of RPMI culture medium, DMEM culture medium, MEM culture medium, F12 culture medium, and α-MEM culture medium, and wherein the stem cells having similar characteristics to those of embryonic stem cells have surface markers specific for embryonic stem cells, have embryonic stem cell specific gene expression, and/or have an ability to form a teratoma.

2. The method of claim 1, further comprising eliminating dead cells adhered to the cardiomyocytes and/or the Brachyury+/Nkx 2.5-cells by treating the cell mixture with a collagenase.

3. The method of claim 2, wherein the dead cells are eliminated based on the filet that the specific gravity of the dead cells is higher than that of the cardiomyocytes and/or the Brachyury+/Nkx2.5-cells.

4. The method of claim 1, wherein the condition (ii) of the culture medium is a lactic acid-supplemented condition.

5. The method claim 1, wherein the condition (ii) of the culture medium is an aspartic acid/glutamic acid-supplemented condition.

6. The method of claim 1, wherein the condition (ii) of the culture medium is a pyruvic acid-supplemented condition.

7. The method of claim 1, wherein the cell mixture is prepared by the following steps of:
inducing differentiation of embryonic stem cells or stem cells having similar characteristics to those of embryonic stem cells in a culture medium;
forming embryoid bodies comprising the Brachyury+/Nkx2.5-cells; and
preparing the cell mixture by culturing the embryoid bodies under a low-serum -supplemented condition and/or a mildly-acidic pH condition, wherein the low-serum -supplemented condition is serum-free condition, or a condition wherein the concentration of serum or serum components is reduced to less than 10% of serum or serum components supplemented to the culture medium used in the step of inducing differentiation.

8. A method for selecting cardiomyocytes and/or Brachyury+/Nkx2.5-cells capable of differentiating into cardiomyocytes derived from embryonic stem cells comprising:
inducing differentiation of embryonic stem cells in a first culture medium to form embryoid bodies comprising the Brachyury+/Nkx2.5-cells;
then preparing a cell mixture comprising the Brachyury+/Nkx2.5-cells by culturing the embryoid bodies in a second culture medium under a low-serum-supplemented condition and a mildly acidic pH condition, wherein the low-serum-supplemented condition is serum-free condition, or a condition wherein the concentration of serum or serum components is reduced to less than 10% of serum or serum components supplemented to the first culture medium used in the process for obtaining the embryoid bodies; and
continuing the culture of the cell mixture in the same culture medium to obtain the cardiomyocytes and/or the Brachyury+/Nkx2.5-cells.

9. The method of claim 1, wherein the low calcium condition is a condition wherein the calcium concentration in the culture medium ranges between 0.3-1.3 mM.

10. The method of claim 1, wherein the lactic acid -supplemented condition is a condition wherein 0.1-5 mM of lactic acid is supplemented to the culture medium.

11. The method of claim 1, wherein the aspartic acid/glutamic acid-supplemented condition is a condition wherein 20-100 mg/L of aspartic acid and 20-100 mg/L of glutamic acid are supplemented to the culture medium.

12. The method of claim 1, wherein the pyruvic acid -supplemented condition is a condition wherein 0.5-5 mM of pyruvic acid is supplemented to the culture medium.

13. The method of claim 7, wherein the mildly-acidic pH condition is a condition of pH 6.5.

14. The method of claim 1, wherein the sugar is glucose.

15. The method of claim 1, wherein the stem cells having similar characteristics to those of embryonic stem cells are embryonic germ cells (EG cells) produced from primordial germ cells, germline stem cells (GS cells) produced from testicular germ cells, or induced pluripotent stem cells (iPS cells) produced from somatic cells.

16. The method of claim 15, wherein the stem cells having similar characteristics to those of embryonic stem cells are induced pluripotent stem cells (iPS cells).

17. The method of claim 7, wherein the concentration of serum or serum components is 0 to 1% in the low-serum-supplemented condition.

18. The method of claim 8, wherein the concentration of serum or serum components is 0 to 1% in the low-serum-supplemented condition.

* * * * *